United States Patent
Kobayashi et al.

(10) Patent No.: US 8,755,117 B2
(45) Date of Patent: Jun. 17, 2014

(54) METHOD OF MANUFACTURING A DIFFRACTION LENS OTHER THAN AN APHAKIC INTRAOCULAR LENS

(75) Inventors: Atsushi Kobayashi, Seto (JP); Hiroaki Suzuki, Tajimi (JP); Ichiro Ando, Kasugai (JP)

(73) Assignee: Menicon Co., Ltd., Nagoya-Shi (JP)

( * ) Notice: Subject to any disclaimer, the term of this patent is extended or adjusted under 35 U.S.C. 154(b) by 225 days.

(21) Appl. No.: 13/142,737

(22) PCT Filed: Jan. 6, 2009

(86) PCT No.: PCT/JP2009/000020
§ 371 (c)(1),
(2), (4) Date: Jun. 29, 2011

(87) PCT Pub. No.: WO2010/079528
PCT Pub. Date: Jul. 15, 2010

(65) Prior Publication Data
US 2011/0267693 A1    Nov. 3, 2011

(51) Int. Cl.
*G02B 5/18*    (2006.01)
(52) U.S. Cl.
USPC .......................................... 359/569; 359/558
(58) Field of Classification Search
None
See application file for complete search history.

(56) References Cited

U.S. PATENT DOCUMENTS

| | | |
|---|---|---|
| 4,881,804 A | 11/1989 | Cohen |
| 4,936,666 A | 6/1990 | Futhey |
| 4,995,714 A | 2/1991 | Cohen |
| 5,056,908 A | 10/1991 | Cohen |
| 5,121,980 A | 6/1992 | Cohen |
| 5,760,871 A | 6/1998 | Kosoburd et al. |
| 6,829,093 B1 | 12/2004 | Nakai |
| 7,188,949 B2 | 3/2007 | Bandhauer et al. |
| 2011/0270390 A1* | 11/2011 | Kobayashi et al. .......... 623/6.38 |

FOREIGN PATENT DOCUMENTS

| | | |
|---|---|---|
| JP | A-01-154119 | 6/1989 |
| JP | A-02-079815 | 3/1990 |
| JP | A-02-137815 | 5/1990 |
| JP | A-03-062001 | 3/1991 |
| JP | U-03-035502 | 4/1991 |
| JP | A-07-198909 | 8/1995 |
| JP | A-2001-042112 | 2/2001 |

OTHER PUBLICATIONS

International Preliminary Report on Patentability issued in Application No. PCT/JP2009/000020; Dated Aug. 16, 2011.
International Search Report issued in Application No. PCT/JP2009/000020; Dated Apr. 7, 2009 (With Translation).

* cited by examiner

*Primary Examiner* — Stephone B Allen
*Assistant Examiner* — Jyotsna Dabbi
(74) *Attorney, Agent, or Firm* — Oliff PLC

(57) ABSTRACT

A novel manufacturing method for a diffraction lens, whereby aperture and eccentricity effects can be suppressed and any multi-focusing effect can also be obtained in a more stable manner. A synchronous structure is set up where at least two reliefs whose first order diffracted lights give respective focal distances different from one another are set to overlap with each other in at least a part of an area in a radial direction of a diffraction lens, and with respect to every grating pitches of one relief having the maximum grating pitch among the reliefs set up in overlap, grating pitches of another relief are overlapped periodically; and the resulting relief pattern is formed on a surface of an optical material.

14 Claims, 15 Drawing Sheets

RELIEF PROFILE (FAR VISION +2.00D & INTERMEDIATE VISION +1.00D)

DIFFRACTION INTENSITY ALONG OPTICAL AXIS (FAR VISION +2.00D & INTERMEDIATE VISION +1.00D)

RELIEF PROFILE (NEAR VISION +3.00D & INTERMEDIATE VISION +1.00D)

DIFFRACTION INTENSITY ALONG OPTICAL AXIS
(NEAR VISION +3.00D & INTERMEDIATE VISION +1.00D)

RELIEF PROFILE (NEAR VISION +4.00D)

RELIEF PROFILE (INTERMEDIATE VISION +2.00D)

RELIEF PROFILE (COMPARATIVE EXAMPLE 2) — COMPARATIVE EXAMPLE 2

METHOD OF MANUFACTURING A DIFFRACTION LENS OTHER THAN AN APHAKIC INTRAOCULAR LENS

TECHNICAL FIELD

This invention relates to a method of manufacturing a diffraction lens and to a diffraction lens with a novel structure that can be favorably manufactured thereby.

BACKGROUND ART

Conventionally, optical lenses such as glasses, contact lenses, camera lenses, and pickup lenses for optical discs including compact discs have been used in various fields. Under these circumstances, lenses having multiple foci (multi-focus lenses) that can accommodate for both far vision and near vision in glasses, contact lenses and the like for presbyopia, for example, are sometimes required.

As such a multi-focus lens, a diffraction lens such as that disclosed in Patent Literature 1, for example, is known to the public. The diffraction lens described in Patent Document 1 is provided with a diffraction grating having a relief on the lens surface, and is allowed to form two foci by the 0th order light and first order diffracted light taking advantage of the diffraction phenomenon of light that passes through the relief. In case of using such a diffraction lens as a bifocal lens for presbyopia, it is made possible to form two foci by means of assigning each focus of the 0th order light and first order diffracted light for far vision and near vision respectively.

However, in recent years, optical lenses with more number of foci are sometimes required. For instance, bifocal lenses assign the 0th order light and first order light for far vision and near vision respectively, as described above, resulting in a problem getting more recognized these days that allocating energy to the mid-section between the 0th order and first order light becomes more difficult and the contrast in the intermediate vision range gets too low.

Therefore, to be able to generate more number of foci, a diffraction lens that produces multiple foci by means of forming multiple areas with a different relief in each area in the lens radial direction is proposed in Patent Document 2, for example. However, the diffraction lens described in Patent Document 2 had a risk of failing to achieve the desired focal effect when the diameter of incident light beam varies by aperture or due to pupil shrinkage of human eyes. Especially in case of an ophthalmic lens, it is not necessarily possible to stably place a diffraction lens in the desired position relative to the pupil, even if it is designed with consideration of physiological pupil diameter of human eyes, which poses a risk of failing to achieve the desired focal effect.

Patent Document 1: U.S. Pat. No. 5,121,980
Patent Document 2: U.S. Pat. No. 7,188,949

SUMMARY OF THE INVENTION

Problem the Invention Attempts to Solve

With the foregoing in view, it is accordingly an object of the present invention, to provide a novel method of manufacturing a diffraction lens that is capable of ensuring every multi-focusing effect more securely, while reducing the impact of aperture changes and lens eccentricity.

Furthermore, this invention aims at providing a diffraction lens with a novel structure which can be favorably manufactured thereby.

Means for Solving the Problem

Modes of this invention contrived to solve the above problems are described in the following paragraphs. Also, the components adopted in each modes described below are adoptable in any other possible combination.

A first mode of this invention relating to a method of manufacturing a diffraction lens (except an aphakic intraocular lens) provides a manufacturing method of a diffraction lens (except an aphakic intraocular lens) provided with a diffraction grating having a relief pattern extending concentrically on a surface of an optical material, comprising the steps of: adopting various types of reliefs whose first order diffracted lights give respective focal distances different from one another for the relief pattern; setting up a synchronous structure where at least two reliefs are set to overlap with each other in at least a part of an area in a radial direction of the diffraction lens, and with respect to every grating pitches of one relief having a maximum grating pitch among the reliefs set up in overlap, grating pitches of another relief are overlapped periodically, in order to obtain the relief pattern; and forming the resulting relief pattern on the surface of the optical material.

According to the manufacturing method of this invention, at least two foci can be generated by each first order diffracted light of at least two reliefs. With this arrangement, in case of using bifocal contact lenses for presbyopia, for example, as an optical material, the 0th order light by the refractive surface of the lens, for example, is set to focus for far vision, while the first order light by one of the two reliefs is set to focus for near vision, in addition to having the other first order light set to focus for intermediate vision. This makes it possible to obtain good diffraction intensity in the intermediate vision range in addition to the far and near vision ranges, thus providing a contact lens capable of delivering good vision in the intermediate range. The word "relief" in this invention refers to a jagged form.

According to the diffraction lens manufactured by the present manufacturing method, various types of reliefs are set to overlap with each other. This allows the first order diffracted light to be generated by each relief in the entire area where various types of reliefs are overlapped. Therefore, unlike a diffraction lens on which different reliefs are set up in each area, as described in the above Patent Document 2 for example, it is now possible to obtain a diffraction lens with an unprecedented new optical properties, whereby the desired optical properties are more securely obtained by restricting relative variations of the diffraction intensity in a particular area caused by changes in diameter of incident light beam following changes in aperture and the eccentricity of the lens and the like.

Besides, especially by the present manufacturing method, a synchronous structure is set up where grating pitches of other reliefs are overlapped periodically with each grating pitch of the relief having the maximum grating pitch among the reliefs set up in overlap. That is, the synchronous structure is set up where zone radii of other reliefs are overlapped periodically with each zone radius of the relief having the maximum grating pitch. Here, the word "grating pitch" means a width of each relief between the ridge and valley lines in the radial direction. The "zone radius" refers to a radius of a ridge or valley line located on the outer side of the concentric center measured from the concentric center in the zone between the ridge and valley lines of each relief extending concentrically. Also, "concentrically" means a state of multiple streaks in forms of circles or something similar such as ovals extending in an annular pattern centered on an optical axis or an eccentric axis. Also, the "radial direction of the diffraction lens" mentioned in the claims of this invention means a radial direction centered on the optical axis, and in case the optical axis is off the geometric center of the lens, it is not necessarily identical to the radial direction of the lens relative to its outer peripheral configuration. This makes it possible to distinctly generate a peak of diffraction intensity of the first order diffracted light of each relief and to obtain a multitude of foci more certainly. In other words simply overlapping various types of reliefs cannot clearly obtain a peak of diffraction intensity of any relief and results in generating peaks of unintended order of light beams, while increasing the quantity of glare caused by stray light beams. On the contrary, according to the present manufacturing method, diffraction intensity can be allocated effectively to the first order diffracted light of other reliefs by synchronizing grating pitches of different relief patterns, thus reducing the intensity of unnecessary nth order diffracted light beams including second order diffracted light. As a result, the quantity of stray light and so forth can be lowered and the glare and the like can be reduced.

Meanwhile, the first order diffracted light in this invention is first order interference light accompanying diffraction and also is diffracted light that generates a phase difference of one wavelength. In other words, since the speed of light is slower in a medium with higher refractive index than that of air, it is the positive first order diffracted light that is the first order interference light obtained by making use of this phenomenon, and by overlapping, in delayed phases by one wavelength, the light beams that pass through reliefs adjacent to each other from the concentric center toward the periphery on a diffraction grating with reliefs having a ridge line on the center side of the concentric circle, and on the contrary, in case of using a diffraction grating with reliefs with their positive and negative reversed having a ridge line on the outer side of the concentric circle, it is the negative first order diffracted light that is the first order interference light generated on the opposite side of the reliefs obtained by overlapping, in advanced phases by one wavelength, the light beams that pass through reliefs adjacent to each other from the center toward the periphery. The "first order light" described in the claims of this invention is to be interpreted as first order light with an absolute value of both the positive first order diffracted light and negative first order diffracted light.

Also in this invention, it is sufficient for various types of reliefs to be set overlapped in at least a part of the area in the radial direction of the lens, and not necessarily to be set overlapped all across the lens surface. Therefore, for example, various types of reliefs may be set overlapped only at the center of the lens or at the intermediate area in the radial direction of the lens, while only one relief may be set in the other part of the area.

Moreover, as various types of reliefs in this invention, at least two types are good enough, and as a matter of course, three or more relief can be set overlapped.

In addition, the manufacturing method of this invention can be broadly applied as a method of manufacturing diffraction lenses used in various fields, except aphakic intraocular lenses set in place in the crystalline capsule, and includes, for example, not only ophthalmic lenses for vision corrections such as glasses, contact lenses, and phakic intraocular lenses such as phakic IOLs to be embedded between the pupil and cornea, and ICLs to be embedded between the pupil and crystalline lens, but also optical lenses used for ophthalmic inspection devices as well as various optical instruments such as cameras and optical disc pickups. Moreover, the cornea can be considered as one of the optical lenses, and it is also possible, for example, to apply the present manufacturing method to surgery operations for reconstruction of the corneal surface by Lasik.

Therefore, as the optical materials for the present invention, translucent materials such as resin, glass, and even corneas can be adopted without particular limitation, and the shapes and materials and so forth of the reference plane where the synchronous structure of the reliefs is formed are not particularly limited. For example, such a reference plane can be a spherical plane, either convex or concave, or an aspheric, cylindrical or toric plane, or even a flat plane. Especially, in case the reference plane is other than a flat plane, the optical refractive property, in addition to the diffraction of this invention, is to be exerted.

KEYS TO SYMBOLS

Figure 1:
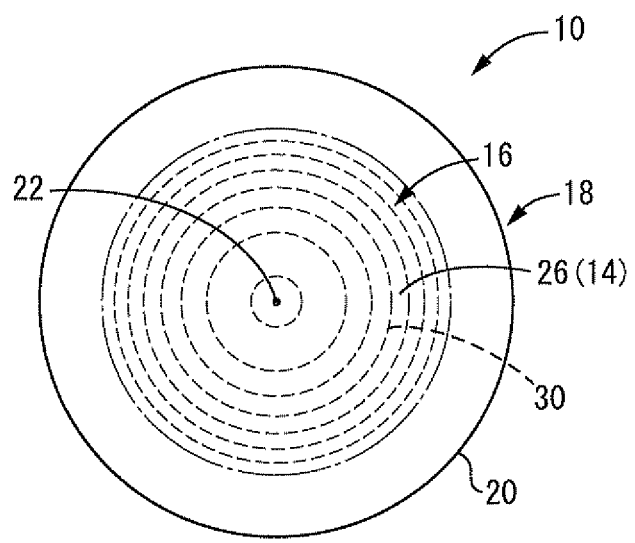
FIG. 1 is a front view diagram showing a diffraction lens as a first embodiment of the present invention.

10: Contact lens, 22: Lens center axis, 24: Rear optical part, 26: Front optical part, 28: Diffraction grating, 30: Relief pattern, 36: Ridge line, 38: Valley line

EMBODIMENTS FOR CARRYING OUT THE INVENTION

A second mode of this invention related to the method of manufacturing a diffraction lens (except an aphakic intraocular lens), according to the first mode, wherein the optical material comprises an optical lens with a refractive surface, and the method further comprises the step of setting a focal distance for a 0th order light by the refractive surface of the lens a focal distance being different from that of any of first order diffracted lights generated by the various types of reliefs.

According to the present mode, it is possible to obtain an optical lens with three or more foci including the focus generated by each first order diffracted light of at least two reliefs as well as the focus of the 0th order light by the refractive surface. The various types of reliefs can be formed on a refractive surface or a plane other than the refractive surface. Therefore, this mode includes an arrangement wherein a relief is formed on the non-refractive side of a lens, one side of which is a curved plane as a concave or convex refractive surface and the other is a plane as a non-refractive surface, and further includes, as a third mode of this invention related to the method of manufacturing a diffraction lens (except an aphakic intraocular lens) according to the second mode, an arrangement wherein the surface of the optical material formed with the relief pattern is the refractive surface.

A fourth mode of this invention related to the method of manufacturing a diffraction lens (except an aphakic intraocular lens) according to the first or second mode, wherein the surface of the optical material formed with the relief pattern is a flat plane.

In the present mode, the surface of the optical material where the relief is formed is considered to be the non-refractive plane. The present mode includes a mode wherein reliefs are formed on both surfaces of an optical lens whose both surfaces are flat planes, that is, non-refractive planes, as well as a mode wherein a relief is formed on a flat plane side of an optical lens whose one-side surface is a flat plane and the other side is a refractive surface.

A fifth mode of this invention related to the method of manufacturing a diffraction lens (except an aphakic intraocular lens) according to one of the first through fourth modes, further comprising the step of setting each relief depth of the relief having the maximum grating pitch, which is obtained by overlapping the various types of reliefs, is made constant in a zone direction.

Here, the word "relief depth" means a height of a relief in the optical axis direction at each zone radius position. According to the present mode, it is rendered unnecessary to set the depth of the relief with the maximum grating pitch for each zone, thus making it easier to set the relief pattern.

A sixth mode of this invention related to the method of manufacturing a diffraction lens (except an aphakic intraocular lens) according to the fifth mode, further comprising the steps of forming in each zone in the relief having the maximum grating pitch another type of relief with at least two relief depths in the area in the radial direction of the lens where the various types of reliefs set up in overlap, and setting dimensions of the at least two relief depths relative to a virtual base curve surface so as to gradually vary in the zone direction.

According to the present mode, the depth of the relief of another type can be set with more accuracy, and the peak of diffraction intensity by the relief of another type can be generated more distinctly. In this mode, the phrase "relief depths relative to the virtual base curve surface are set to gradually vary in the zone direction" includes modes where the depth gradually increases and decreases.

A seventh mode of this invention related to the method of manufacturing a diffraction lens (except an aphakic intraocular lens) according to the fifth mode, further comprising the steps of forming in each zone in the relief having the maximum grating pitch another type of relief with at least two relief depths in the area in the radial direction of the lens where the various types of reliefs set up in overlap, and setting dimensions of the at least two relief depths relative to the virtual base curve surface so as to be constant in the zone direction. According to the present mode, it is rendered unnecessary to set the form of another type of relief per each zone radius, thus making it easier to set the form of another type of relief.

An eighth mode of this invention related to the method of manufacturing a diffraction lens (except an aphakic intraocular lens) according to one of the first through seventh modes, wherein each of the various types of reliefs has a ridge line extending circumferentially with a cross-section formed with an acute vertex angle and a valley line extending circumferentially with a cross-section formed with an acute included angle.

According to the present mode, it is now possible to effectively generate diffraction effects in each of multiple reliefs and effectively generate a peak for the first order diffracted light of each type of relief.

A ninth mode of this invention related to the method of manufacturing a diffraction lens (except an aphakic intraocular lens) according to one of the first through eighth modes, wherein the optical material comprises a cornea.

Namely, the cornea can be considered as one of the optical lenses, and it is also possible, for example, to apply the present manufacturing method to surgery operations for reconstruction of the corneal surface by Lasik and provide the corneal surface with a relief pattern where a synchronous structure is set like the one in this invention.

A tenth mode of this invention related to the method of manufacturing a diffraction lens (except an aphakic intraocular lens) according to one of the first through ninth modes, wherein the optical material comprises an ophthalmic lens with a refractive surface, and the method further comprises the steps of: setting to the 0th order light by the refractive surface of the lens a focus for far vision; setting to the first order diffracted light by one type of the relief a focus for near vision; and setting to the first order diffracted light by another type of the relief a focus for intermediate vision.

According to the present mode, it is now possible to obtain an ophthalmic lens having a focus for intermediate vision in addition to far vision and near vision. Therefore, the conventional problem of lowered contrast for intermediate vision with ophthalmic lenses of diffraction type such as glass lenses and contact lenses for correction of presbyopia can be improved, thus making it possible to obtain better intermediate vision.

A eleventh mode of this invention related to the method of manufacturing a diffraction lens (except an aphakic intraocular lens) according to one of the first through ninth modes, wherein the optical material comprises the ophthalmic lens with the refractive surface, and the method further comprises the steps of: setting to the 0th order light by the refractive surface of the lens a focus for near vision; setting to the first order diffracted light by one type of the relief a focus for far vision; and setting to the first order diffracted light by another type of the relief a focus for intermediate vision.

Also in the present mode, it is now possible to obtain an ophthalmic lens that can achieve better intermediate vision. Here, in this mode, both near vision focus and far vision focus turn out to be the ones of the negative first order light by the corresponding relief, but as described above, the first order light in this invention is to be interpreted as first order light with an absolute value including the negative first order light.

A twelfth mode of this invention related to the method of manufacturing a diffraction lens (except an aphakic intraocular lens) according to one of the first through eleventh modes, wherein the optical material comprises the ophthalmic lens with the refractive surface, the method further comprises the steps of: setting on the refractive surface the diffraction grating composed of the various types of reliefs, the refractive surface being in a concave shape, and in at least one type of the reliefs in a radial cross-section, setting an inclination direction between zones outward along a lens axis in a same direction as a protrusion of the relief depth.

The present mode is favorably used for contact lenses, for example. Namely, the contact lens's rear surface is a refractive surface, that is made in a concave shape opposing the cornea, and a relief pattern is formed on such rear surface of the lens.

A thirteenth mode of this invention related to the method of manufacturing a diffraction lens (except an aphakic intraocular lens) according to one of the first through twelfth modes, wherein the various types of reliefs are arranged to satisfy a following equation:

$$A=(2(m-NM)+a)/N$$

where A is a zone constant of the one relief, 'a' is a zone constant of the other relief, M is a zone number of the one relief, m is a zone number of the other relief, and N is a ratio of a focal distance of the one relief relative to that of the other relief, which is expressed as:

(focal distance of the one relief)/(focal distance of the other relief).

Here, the "zone constant" means a constant for setting a zone radius of a given zone number at a certain value, and the zone radius is given by the following equation using the zone constant 'a':

$$\text{Zone radius}=((2m+a)\lambda f)^{(1/2)}$$

where $\lambda$ is the design wavelength, and f is a focal distance. Also, the "zone number" refers to a number allocated for each zone in the order of 1, 2, 3, . . . from the center at 0 outward in the zone direction.

According to the present mode, it is easy to set up a synchronous structure where a grating pitch of the other relief is overlapped periodically with that of the one relief.

A fourteenth mode of this invention related to the method of manufacturing a diffraction lens (except an aphakic intraocular lens) according to one of the first through thirteenth modes, wherein the various types of reliefs are arranged to satisfy a following equation:

$$D \leq \lambda \times /(N_{lens}-N_{med})$$

where D is a dimension of the relief depth, $\lambda$ is a design wavelength, $N_{lens}$ is a refractive index of the optical material, and $N_{med}$ is a refractive index of a surrounding medium.

According to the present mode, the maximum relief depth is equal to one wavelength, which makes it possible to more securely facilitate the allocation of the 0th order light and first order light. Therefore, the present mode is preferably used in combination with other modes such as the above third mode, wherein the relief pattern is formed on the refractive surface. With this arrangement, intensity of unnecessary nth order light such as the second order light can be reduced, and the focal effects of the 0th order light and first order light can be effectively produced.

Another aspect of the present invention relates to a diffraction lens (except an aphakic intraocular lens). A first mode of the invention related to the diffraction lens provides a diffraction lens (except an aphakic intraocular lens) provided with a diffraction grating having a relief pattern extending concentrically on a surface of an optical material, comprising: a synchronous structure where various types of reliefs including at least two reliefs whose first order diffracted lights give respective focal distances different from one another are set to overlap with each other in at least a part of an area in a radial direction of the lens, and with respect to every grating pitches of one relief having a maximum grating pitch among the reliefs set up in overlap, grating pitches of another relief being overlapped periodically.

According to the diffraction lens of the present mode, at least two foci can be generated by each first order diffracted light of at least two reliefs. This makes it possible to obtain a focus for far vision of the 0th order light by the refractive surface, for example, in case of using bifocal contact lenses for presbyopia as the optical material, while obtaining a focus for near vision of the first order light by one of the two reliefs, in addition to obtaining a focus for intermediate vision by the other first order light. This makes it possible to obtain good diffraction intensity in the intermediate vision range in addition to the far and near vision ranges, thus providing contact lenses capable of delivering good vision in the intermediate range. The word "relief" in this invention refers to a jagged form.

Especially according to the diffraction lens of the present mode, the various types of reliefs are set overlapped. This allows the first order diffracted light to be generated by each relief in the entire area where various types of reliefs are overlapped, and therefore, unlike a diffraction lens on which different reliefs are set up in each area, as described in the above Patent Document 2 for example, it is now possible to restrict relative variations of the diffraction intensity in a specific area caused by changes in diameter of incident light beam following aperture changes and eccentricity of the lens and the like, thus enabling to obtain an diffraction lens with an unprecedented new optical properties whereby the desired optical properties are more securely obtained.

Moreover, in the present mode, a synchronous structure is set up where grating pitches of other reliefs are overlapped periodically with each grating pitch of the relief having the maximum grating pitch among the reliefs set up in overlap, that is, zone radii of other reliefs are overlapped periodically with each zone radius of the relief having the maximum grating pitch. The word "concentrically" means a state of multiple streaks in forms of circles or something similar such as ovals extending in an annular pattern centered on an optical axis or an eccentric axis. Also, the "radial direction of the diffraction lens" mentioned in the claims of this invention means a radial direction centered on the optical axis, and in case the optical axis is off the geometric center of the lens, it is not necessarily identical to the radial direction of the lens relative to its outer peripheral configuration. This makes it possible to distinctly generate a peak of diffraction intensity of the first order diffracted light of each relief and to obtain a multitude of foci more certainly. In other words simply overlapping various types of reliefs cannot clearly obtain a peak of diffraction intensity of any relief and results in generating peaks of unintended order of light beams while increasing the quantity of glare caused by stray light beams. On the contrary, according to the diffraction lens in the present mode, diffraction intensity can be allocated effectively to the first order diffracted light of other reliefs by synchronizing grating pitches of different types of relief, thus reducing the intensity of unnecessary nth order diffracted light including second order diffracted light. As a result, light intensity of stray light beams and so forth can be lowered and the glare and the like can be reduced.

Also in the present mode, it is sufficient for various types of reliefs to be set overlapped in at least a part of the area in the radial direction of the lens, and not necessarily to be set overlapped all across the lens surface. Therefore, for example, various types of reliefs can be set overlapped only at the center of the lens or at the intermediate area in the radial direction of the lens, while only one relief can be set in the other part of the area.

Furthermore, as various types of reliefs in the present mode, at least two types are good enough, and as a matter of course, three or more types of reliefs can be set overlapped.

In addition, the diffraction lens in the present mode can be broadly applied as one of the diffraction lenses used in various fields, except aphakic intraocular lenses set in place in the crystalline capsule, and includes, for example, not only ophthalmic lenses for vision corrections such as glasses, contact lenses, phakic IOLs to be embedded between the pupil and cornea, and phakic intraocular lenses such as ICLs to be embedded between the pupil and crystalline lens, but also optical lenses used for ophthalmic inspection devices as well as various optical instruments such as cameras and optical disc pickups.

Therefore, as the optical materials for the present mode, translucent materials such as resin and glass can be adopted without particular limitation, and the shapes and materials and so forth of the reference plane where the synchronous structure of the reliefs is formed are not particularly limited. For example, such a reference plane can be a spherical plane, either convex or concave, or an aspheric, cylindrical or toric plane, or even a flat plane. Especially, in case the reference plane is other than a flat plane, the optical refractive property, in addition to the diffraction of this mode, is to be exerted.

The second mode of this invention related to the diffraction lens (except an aphakic intraocular lens) according to the first mode, wherein the optical material comprises an optical lens with a refractive surface, and a focal distance different from that of any first order diffracted light generated by the various types of reliefs is set for a 0th order light by the refractive surface of the lens.

According to the present mode, it is possible to obtain an optical lens with three or more foci including the foci generated by each first order diffracted light of at least two reliefs as well as the focus of the 0th order light by the refractive surface. In this situation, the various types of reliefs can be formed on a refractive surface or a plane other than the refractive surface. Therefore, this mode includes an mode wherein one side is a curved plane as a concave or convex refractive surface and the other is a plane as a non-refractive surface where a relief is formed on the non-refractive side, and further includes, as a third mode of this invention related to a diffraction lens (except an aphakic intraocular lens), an mode wherein the surface of the optical material formed with the relief pattern is the refractive surface.

A fourth mode of this invention related to a diffraction lens (except an aphakic intraocular lens) according to the first or second mode, wherein the surface of the optical material formed with the relief pattern is a flat plane.

In the present mode, the surface of the optical material where a relief is formed is considered to be the non-refractive plane. The present mode includes an mode wherein reliefs are formed on the surface of the optical lens with its both sides being flat planes, that is, non-refractive planes, as well as an mode wherein a relief is formed on the flat plane side with the other side being a refractive surface.

A fifth mode of this invention related to a diffraction lens (except an aphakic intraocular lens) according to one of the first through fourth modes, wherein each relief depth of the relief having the maximum grating pitch, which is obtained by overlapping the various types of reliefs, is made constant in a zone direction.

Here, the word "relief depth" means a height of a relief at each zone radius position in the optical axis direction. According to the present mode, it is rendered unnecessary to set the depth of the relief with the maximum grating pitch for each zone, thus making it easier to set the relief pattern and to manufacture the products.

A sixth mode of this invention related to a diffraction lens (except an aphakic intraocular lens) according to the fifth mode, wherein in each zone in the relief having the maximum grating pitch, another type of relief with at least two relief depths is formed in the area in the radial direction of the lens where the various types of reliefs set up in overlap, and dimensions of the at least two relief depths relative to a virtual base curve surface vary gradually in the zone direction.

According to the present mode, the depth of the relief of another type can be set with more accuracy, and the peak of diffraction intensity by the relief of another type can be generated more distinctly. Here, in this mode, the phrase "relief depths relative to the virtual base curve surface are set to gradually vary in the zone direction" includes modes where the depth gradually increases and decreases.

A seventh mode of this invention related to a diffraction lens (except an aphakic intraocular lens) according to the fifth mode, wherein in each zone in the relief having the maximum grating pitch, another type of relief with at least two relief depths is formed in the area in the radial direction of the lens where the various types of reliefs set up in overlap, and dimensions of the at least two relief depths relative to the virtual base curve surface are set constant in the zone direction. According to the present mode, it is rendered unnecessary to set the form of another type of relief per each zone radius, thus making it easier to set the form of another type of relief.

An eighth mode of this invention related to a diffraction lens (except an aphakic intraocular lens) according to one of the first through seventh modes, wherein each of the various types of reliefs has a ridge line extending circumferentially with a cross-section formed with an acute vertex angle and a valley line extending circumferentially with a cross-section formed with an acute included angle.

According to the present mode, it is now possible to effectively generate diffraction effects in each of various types of reliefs and effectively generate a peak for the first order diffracted light of each type of relief.

A ninth mode of this invention related to a diffraction lens (except an aphakic intraocular lens) according to one of the first through eighth modes, wherein the optical material comprises an ophthalmic lens with a refractive surface, the 0th order light by the refractive surface of the lens is set to a focus for far vision, the first order diffracted light by one type of the relief is set to a focus for near vision, and the first order diffracted light by another type of the relief is set to a focus for intermediate vision.

According to the present mode, it is now possible to obtain an diffraction lens having a focus for intermediate vision in addition to far vision and near vision. Therefore, the conventional problem of lowered contrast for intermediate vision with ophthalmic lenses of diffraction type such as glass lenses and contact lenses for correction of presbyopia can be improved, thus making it possible to obtain better intermediate vision.

A tenth mode of this invention related to a diffraction lens (except an aphakic intraocular lens) according to one of the first through eighth modes, wherein the optical material comprises the ophthalmic lens with the refractive surface, the 0th order light by the refractive surface of the lens is set to a focus for near vision, the first order diffracted light by one type of the relief is set to a focus for far vision, and the first order diffracted light by another type of the relief is set to a focus for intermediate vision.

Also in the present mode, it is now possible to obtain an ophthalmic lens having a focus for better intermediate vision. Here, in this mode, both near vision focus and far vision focus turn out to be the ones of the negative first order light by the corresponding relief, but as described above, the first order light in this invention is to be interpreted as first order light with an absolute value including the negative first order light.

An eleventh mode of this invention related to a diffraction lens (except an aphakic intraocular lens) according to one of the first through tenth modes, wherein the optical material comprises the ophthalmic lens with the refractive surface, the diffraction grating composed of the various types of reliefs is set on the refractive surface, the refractive surface being in a concave shape, and in at least one type of the reliefs in a radial cross-section, an inclination direction between zones is set outward along a lens axis in a same direction as a protrusion of the relief depth.

The present mode is favorably used for contact lenses, for example. Namely, the contact lens's rear surface is used as a refractive surface, that is made in a concave shape opposing the cornea, and a relief is formed on such rear surface of the lens.

A twelfth mode of this invention related to a diffraction lens (except an aphakic intraocular lens) according to one of the first through eleventh modes, wherein the various types of reliefs are arranged to satisfy a following equation:

$$A=(2(m-NM)+a)/N$$

where A is a zone constant of the one relief, 'a' is a zone constant of the other relief, M is a zone number of the one relief, m is a zone number of the other relief, and N is a ratio of a focal distance of the one relief relative to that of the other relief, which is expressed as:

(focal distance of the one relief)/(focal distance of the other relief).

Here, the "zone constant" means a constant for setting a zone radius of a given zone number at a certain value, and the zone radius is given by the following equation using the zone constant 'a':

$$\text{Zone radius}=((2m+a)\lambda f)^{(1/2)}$$

where $\lambda$ is the design wavelength, and f is a focal distance. Also, the "zone number" refers to a number allocated for each zone in the order of 1, 2, 3, . . . from the center at 0 outward in the zone direction.

According to the present mode, it is easy to set up a synchronous structure where a grating pitch of the other relief is overlapped periodically with that of the one relief.

A thirteenth mode of this invention related to a diffraction lens (except an aphakic intraocular lens) according to one of the first through twelfth modes, wherein the various types of reliefs are arranged to satisfy a following equation:

$$D \leq \lambda/(N_{lens}-N_{med})$$

where D is a dimension of the relief depth, $\lambda$ is a design wavelength, $M_{lens}$ is a refractive index of the above optical material, and $N_{med}$ is a refractive index of a surrounding medium.

According to the present mode, the maximum relief depth is equal to one wavelength, which makes it possible to more securely facilitate the allocation of the 0th order light and first order light. Therefore, the present mode is preferably used in combination with other modes such as the above third mode, wherein the relief pattern is formed on the refractive surface. This way, intensity of unnecessary nth order light such as the second order light can be reduced, and the focal effects of the 0th order light and first order light can be effectively produced.

To further illustrate this invention more specifically, its embodiments will be described in detail below referring to each figures.

Figure 2:
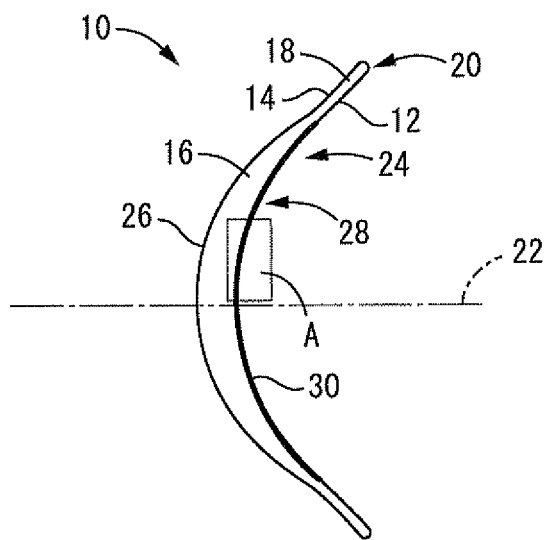
FIG. 2 is a side view of the diffraction lens.

First of all, FIG. 1 shows a front view diagram of a contact lens 10 as a first embodiment related to the diffraction lens in this invention, and FIG. 2 shows a side view of the contact lens 10. Here in FIGS. 1 and 2, a relief pattern 30 described later is shown with its size exaggerated for better understanding.

The contact lens 10 comprises a lens's rear surface 12 in an approximate concave shape of a sphere as a whole and a lens's front surface 14 with an approximate convex shape of a sphere as a whole, and is, in its entirety, in an approximate shape of a spherical shell. Also, the center part of the contact lens 10 is made to be an optical part 16 in a round shape in front view, which can exert the effect of prescribed vision corrections on the wearer. Furthermore, the peripheral part of the contact lens 10 located around the optical part 16 is made to be a peripheral part 18 in an annular shape in front view, which securely holds the contact lens 10 at a given position on the wearer's cornea. Also, the outer edge of the peripheral part 18 is made to be an edge part 20 that connects the inside and outside of the lens. In addition, especially in the present embodiment, the entire contact lens 10 including the optical part 16 and peripheral part 18 is formed as a solid of revolution, both optically and geometrically, formed around a geometric lens center axis 22 as a rotation axis of the contact lens 10.

Besides, in such contact lens 10, the lens's rear surface 12 of the optical part 16 is made to be a rear optical part 24, while the lens's front surface 14 of the optical part 16 is made to be a front optical part 26. The rear optical part 24 has its center of curvature set on the lens center axis 22 toward the back of the lens so as to form a similar shape to that of the wearer's cornea, and constitutes a base curve surface having a concave longitudinal cross-section with proper curvature radius. On the contrary, the front optical part 26 has a curved convex shape that gives desired optical properties such as lens's dioptric power in cooperation with the base curve surface set as mentioned above.

Meanwhile, the contact lens 10 related to the present embodiment is applicable as various contact lenses such as soft or hard contact lenses, or disposable-type contact lenses. Also, as optical materials composing the contact lens 10, resin materials made from various kinds of polymerized monomers having optical properties such as optical transparency and so forth are preferably adopted, which are exemplified more specifically by hydroxyethylmethacrylate (HEMA), polymethylmethacrylate (PMMA), cellulose acetate butyrate (CAB), silicone copolymer, fluorosilicone acrylate, fluorocarbon polymer, and silicone rubbers.

As evident from the above descriptions, in the present embodiment, the rear optical part 24 and front optical part 26 are made to be refractive surfaces, and the contact lens 10 as an optical lens provided with these rear optical part 24 and front optical part 26 is used as an optical material. Then, a given focal distance is set for the 0th order light by these rear optical part 24 and front optical part 26.

Figure 3:
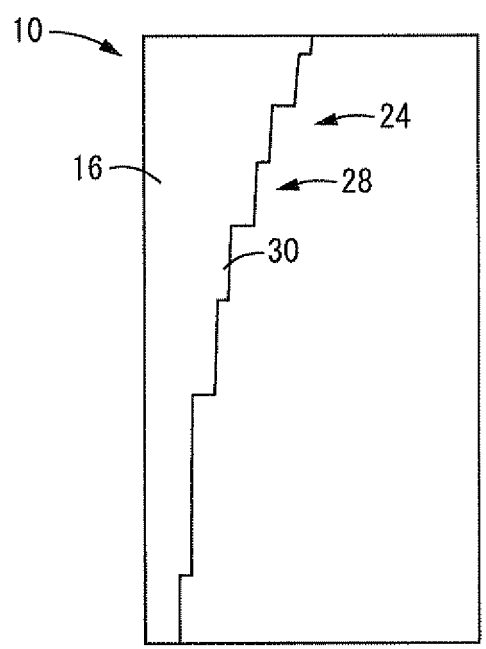
FIG. 3 is an enlarged view diagram of the area A in FIG. 2.

And, as shown in FIG. 3 as an enlarged view diagram of the area A in FIG. 2, a diffraction grating 28 is formed especially on the rear optical part 24 of the present embodiment. The diffraction grating 28 comprises a relief pattern 30 in a jagged form extending concentrically around the lens center axis 22 and continuously toward the periphery of the lens.

Figure 4:
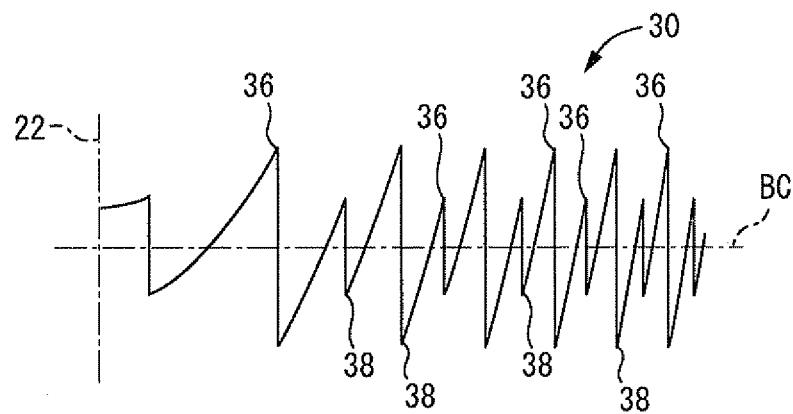
FIG. 4 is a cross-section diagram for explaining a form of a relief pattern provided on the diffraction lens shown in FIG. 1.
Figure 5:
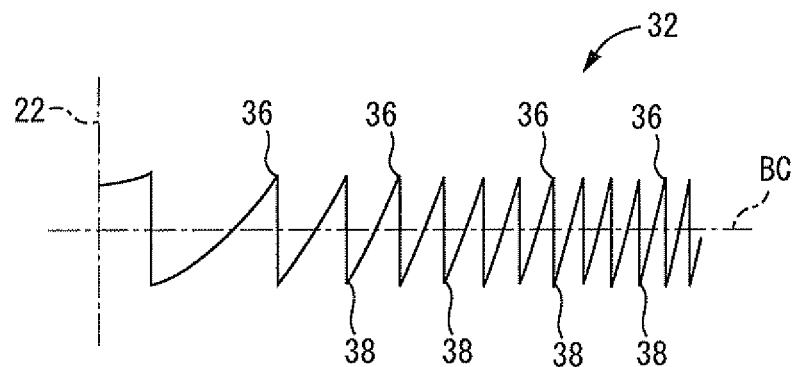
FIG. 5 is a cross-section diagram for explaining a form of a relief for near vision, which composing the relief pattern.
Figure 6:
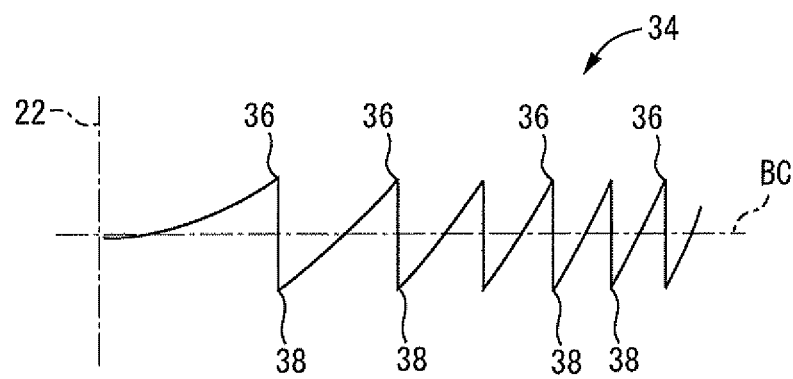
FIG. 6 is a cross-section diagram for explaining a form of a relief for intermediate vision, which composing the relief pattern.

FIG. 4 shows a cross-section diagram of the relief pattern 30 in the radial direction. Especially the relief pattern 30 of the present embodiment is formed by an overlap of a relief 32 for near vision shown in FIG. 5 as a cross-section diagram in the radial direction and a relief 34 for intermediate vision shown in FIG. 6 as a cross-section diagram in the radial direction. These FIGS. 4 through 6 are relief profiles that show changes in height of each of the relief pattern 30 and the reliefs 32, 34, in the lens radial direction, measured from the base curve surface assuming that the base curve surface of the rear optical part 24 is the line BC.

These relief 32 for near vision and relief 34 for intermediate vision are each extending concentrically around the lens center axis 22, and is made in a jagged form having a ridge line 36 protruding outward (upward in FIGS. 4 through 6) from the contact lens 10 and a valley line 38 protruding inward (downward in FIGS. 4 through 6) of the contact lens 10.

In the following descriptions, "grating pitch" means a width between the ridge line 36 and valley line 38 in the radial direction. "Zone" means an area between the ridge line 36 and valley line 38, and a zone number is allocated for each zone in the order of 1, 2, 3 ... from the center at 0 outward in the zone direction. Also, "zone radius" means an outer peripheral radius in each zone, that is, a radius of the ridge line 36 or valley line 38 in each zone located on the outer side of the concentric circle measured from the center of the concentric circle (lens center axis 22 in the present embodiment). Therefore, "grating pitch" is a width of each zone in the radial direction, and grating pitch of a given zone is a difference between the zone radius of said zone and the zone radius of the zone numbered one less. Also, "relief depth" is a separation distance between the ridge line 36 and valley line 38 in the optical axis direction at a zone radius position.

Especially in the present embodiment, the ridge line 36 extends toward the periphery of the contact lens 10 with a cross-section formed with an acute vertex angle, while the valley line 38 is formed to extend toward the periphery of the contact lens 10 with a cross-section with an acute included angle. These relief 32 for near vision and relief 34 for intermediate vision are each in a jagged form, wherein the ridge line 36 and valley line 38 are formed right next to each other in the lens radial direction with the ridge line 36 positioned farther from the lens center axis 22, whereas the farther side to the lens center axis 22, as opposed to the nearer side, is made protruded from the rear optical part 24 in each zone.

These relief 32 for near vision and relief 34 for intermediate vision are set in such a way that each of their first order diffracted light gives a different focal distance from each other, and in the present embodiment, a refractivity of +2.00 D is given to the relief 32 for near vision so as to set the first order diffracted light by the relief 32 for near vision to focus for near vision, while a refractivity of +1.00 D is given to the relief 34 for intermediate vision so as to set the first order diffracted light by the relief 34 for intermediate vision to focus for intermediate vision. In addition, focal distances of the 0th order light by the rear optical part 24 and front optical part 26 are made different from those of the first order diffracted light of any of these relief 32 for near vision and relief 34 for intermediate vision, and the 0th order light by the rear optical part 24 and front optical part 26 is set to focus for far vision.

Then, the relief pattern 30 is formed by having these relief 32 for near vision and relief 34 for intermediate vision set to overlap with each other. In that situation, the grating pitch of the relief 34 for intermediate vision is made larger than that of the relief 32 for near vision, and a synchronous structure is set up where the grating pitch in each zone of the relief 32 for near vision is overlapped periodically with that in each zone of the relief 34 for intermediate vision. This allows the zone radius in each zone of the relief 32 for near vision to be overlapped periodically with that in each zone of the relief 34 for intermediate vision. Especially in the present embodiment, one relief depth of the relief 32 for near vision is formed in one of the zones of the relief 34 for intermediate vision, and two zones of the relief 32 for near vision are formed in one of the zones of the relief 34 for intermediate vision. In other words, each one zone of the relief 34 for intermediate vision is overlapped with two zones of the relief 32 for near vision.

In addition, these relief 32 for near vision and relief 34 for intermediate vision are set to satisfy the following equation:

$$A=(2(m-NM)+a)/N$$

where A is a zone constant of the relief 34 for intermediate vision, 'a' is a zone constant of the relief 32 for near vision, M is a zone number of the relief 34 for intermediate vision, m is a zone number of the relief 32 for near vision, and N is a ratio of the focal distance of the relief 34 for intermediate vision relative to that of the relief 32 for near vision, which is expressed as:

(Focal distance of the relief 34 for intermediate vision)/(Focal distance of the relief 32 for near vision).

This allows a synchronous structure to be set where the relief 32 for near vision and relief 34 for intermediate vision are periodically overlapped. Here, the zone constants A and 'a' are those for setting a zone radius of a certain zone number at a given value, and the zone radius is determined by the following equation using the zone constant 'a':

$$\text{Zone radius}=((2m+a)\lambda f)^{(1/2)}$$

where $\lambda$ is the design wavelength, and f is a focal distance.

Furthermore, these relief 32 for near vision and relief 34 for intermediate vision are each set to satisfy the following equation:

$$D \leq \lambda/(N_{lens}-N_{med})$$

where D is a dimension of the relief depth, λ is the design wavelength, $N_{lens}$ is a refractive index of the lens material, and $N_{med}$ is a refractive index of the surrounding medium. This makes it possible to more effectively facilitate the allocation of the 0th order light and first order light in each of the relief 32 for near vision and relief 34 for intermediate vision. Then, the relief depth of the relief pattern 30 at the position where the relief 32 for near vision and relief 34 for intermediate vision overlap with each other turns out to be a composition of the relief depths of these reliefs 32 and 34. Moreover, especially in the present embodiment, each relief depth of the relief 34 for intermediate vision overlapped with the relief 32 for near vision is made constant in the zone direction (right-left direction in FIG. 4).

In addition, the diffraction grating 28 is formed by having the relief pattern 30 made by overlapping these relief 32 for near vision and relief 34 for intermediate vision formed on the base curve surface of the rear optical part 24. Since the rear optical part 24 is made to be a base curve surface in a concave shape, the relief pattern 30 of the present embodiment sets, as shown in FIG. 3, the inclination direction between the zones outward along the lens axis in the same direction as the protrusion of the relief depth (to the right in FIG. 3).

According to the contact lens 10 with such a structure, the 0th order light of the rear optical part 24 and front optical part 26 gives a focus for far vision, while the first order diffracted light of the relief 32 for near vision gives a focus for near vision, and further, the first order diffracted light of the relief 34 for intermediate vision gives a focus for intermediate vision. This makes it possible to obtain a focus for intermediate vision in addition to far vision and near vision, thus enabling to obtain sufficient quantity of light and clearer contrast for intermediate vision.

Figure 7:
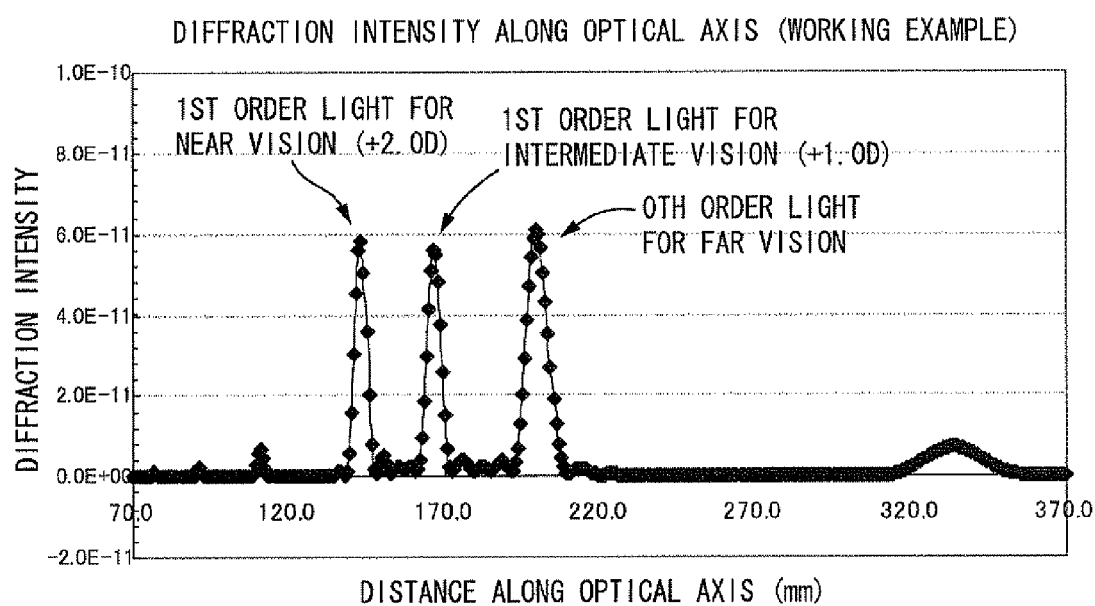
FIG. 7 is a graph showing a simulation result of diffraction intensity in the relief pattern.

Also, FIG. 7 shows, as a working example, a result of computer simulation of diffraction intensity along the optical axis obtained by a relief form according to the present embodiment. As evident from FIG. 7, according to this working example, it can be seen that a peak of diffraction intensity appears at the focus for intermediate vision of the first order diffracted light by the relief 34 for intermediate vision between the focus for far vision of the 0th order light by the rear optical part 24 and front optical part 26 as refractive surfaces and the focus for near vision of the first order diffracted light by the relief 32 for near vision. It can also be seen that a peak is clearly generated in each of far, near and intermediate vision ranges.

Then, especially in the present embodiment, since the relief pattern 30 is formed by an overlap of the relief 32 for near vision and relief 34 for intermediate vision, each first order diffracted light is formed in the entire range of the relief pattern 30. This makes it possible to restrict relative variations of the diffraction intensity in a particular area caused by changes in diameter of incident light beam following pupil shrinkage and eccentricity of the contact lens 10 and the like, thus enabling to obtain desired optical properties more securely.

Additionally, especially in the relief pattern 30 of the present embodiment, the relief 32 for near vision and relief 34 for intermediate vision are formed in a synchronous structure where their grating pitches overlap periodically with each other. This makes it possible to clearly obtain a peak of each first order diffracted light of the relief 32 for near vision and relief 34 for intermediate vision, thus decreasing the quantity of light such as stray light and reducing the glare and the like.

Figure 8:
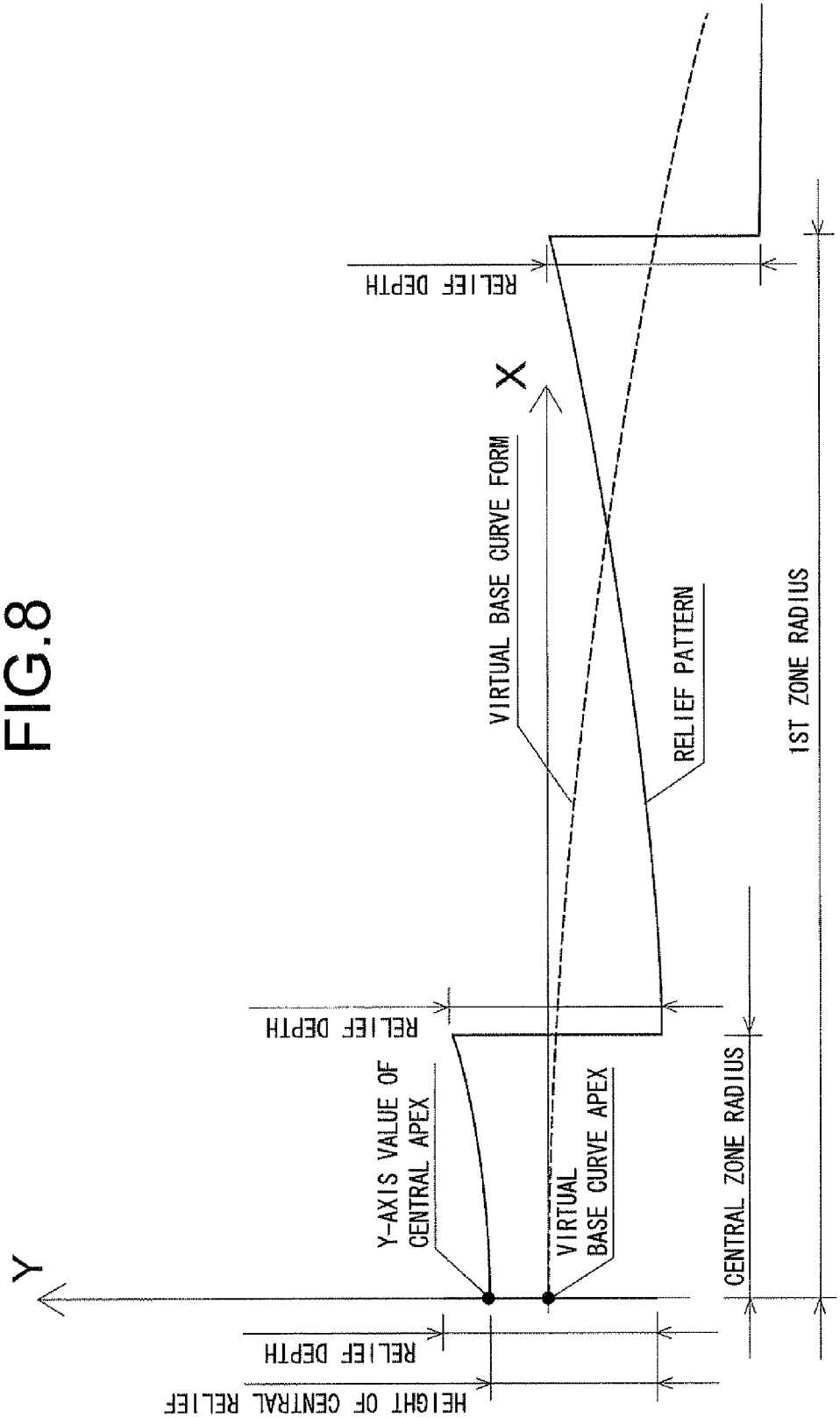
FIG. 8 is a diagram for explaining a design method of the relief pattern.

Next, a method of manufacturing a diffraction lens (except an aphakic intraocular lens) that can be favorably used in manufacturing the contact lens 10 such as the one mentioned above will be described below in reference to FIG. 8.

First of all, forms of the rear optical part 24 and front optical part 26 where the 0th order light generates a focus for far vision are designed as refractive surfaces. In this situation, the focal distance of the 0th order light by the rear optical part 24 and front optical part 26 is set at a distance different from the focal distance of the first order light of either the relief 32 for near vision or relief 34 for intermediate vision. A conventionally known method can be adopted, as appropriate, in the design of such rear optical part 24 and front optical part 26.

Next, the form of the relief 32 for near vision with the dioptric power at +2.00 D is designed. The relief depth is generally determined by the following equation:

$$\text{Relief depth} = p/(n \text{ lens} - n \text{ med}) \quad (1)$$

where p is a phase difference, n lens is a refractive index of the lens material, and n med is a refractive index of the surrounding medium.

Here, the relief depth is desirably a phase difference of no more than one wavelength considering the allocation to the 0th order light that generates far vision, and more preferably, is equal to or smaller than a phase difference of half the wavelength. Then, assuming that λ is the design wavelength and, for example, p=λ/3, n lens=1.500, n med=1.336, λ=500 nm, the following value is obtained:

$$\text{Relief depth} = (0.0005/3)/(1.500 - 1.336)$$
$$= 0.001016260163$$

Next, depending on the intended use of the diffraction lens, and for example, if it is for the contact lens of the present embodiment, the zone radius of the central zone (zone number=0) is determined upon consideration of the pupil radius and zone pitch. For example, the radius of the central zone is set small enough at 0.2 mm compared to the pupil radius. A diffraction formula with the central zone radius set at any value is given by modifying the following equation;

$$\text{Zone radius} = (2m\lambda f)^{(1/2)} \quad (2)$$

into the following equation;

$$\text{Zone radius} = ((2m+a)\lambda f)^{(1/2)} \quad (3)$$

where m is a zone number, λ is the design wavelength, f is a focal distance (f=1,000/power), and 'a' is a zone constant.

Therefore, assuming that the central zone radius is 0.2 mm, the zone constant 'a' can be determined by the following equation;

$$0.2 = ((2 \times 0 + a)0.0005 \times 500)^{(1/2)}$$

and therefore a=0.16, and consequently, an equation is given as follows to calculate the zone radius with the central zone radius set at 0.2 mm:

$$\text{Zone radius} = ((2m+0.16)\lambda f)^{(1/2)} \quad (4)$$

As evident from the equation (3), an increment of the zone constant 'a' by 2 corresponds to an increment of the zone number by one. Therefore, the height of the central relief is determined as follows:

$$\text{Height of central relief} = \text{relief depth} \times (a/2)$$

= 0.00093495935

Besides, since the midpoint of the relief depth is where it intersects with the virtual base curve, the Y-axis value of the central apex is determined as follows on a coordinate system with its origin at the base curve apex:

Y-axis value of central apex = height of central relief − (relief depth/2)

= 0.00093495935 − (0.001016260163/2)

= 0.0004268292685

TABLE 1

Relief for near vision

| Zone No. | Curvature radius of virtual base curve | Zone origin (X-axis) | Zone terminal (X-axis) | Curvature center of Zone (Y-axis) | Zone curvature radius |
|---|---|---|---|---|---|
| 0 | 8 | 0.0000000 | 0.2000000 | 7.7491563 | 7.7481497 |
| 1 | 8 | 0.2000000 | 0.7348469 | 7.7510942 | 7.7497452 |
| 2 | 8 | 0.7348469 | 1.0198039 | 7.7530324 | 7.7526860 |
| 3 | 8 | 1.0198039 | 1.2409674 | 7.7549710 | 7.7556149 |
| 4 | 8 | 1.2409674 | 1.4282857 | 7.7569100 | 7.7585317 |
| 5 | 8 | 1.4282857 | 1.5937377 | 7.7588493 | 7.7614364 |
| 6 | 8 | 1.5937377 | 1.7435596 | 7.7607890 | 7.7643291 |
| 7 | 8 | 1.7435596 | 1.8814888 | 7.7627291 | 7.7672096 |
| 8 | 8 | 1.8814888 | 2.0099751 | 7.7646695 | 7.7700779 |
| 9 | 8 | 2.0099751 | 2.1307276 | 7.7666104 | 7.7729340 |
| 10 | 8 | 2.1307276 | 2.2449944 | 7.7685515 | 7.7757778 |
| 11 | 8 | 2.2449944 | 2.3537205 | 7.7704931 | 7.7786094 |
| 12 | 8 | 2.3537205 | 2.4576411 | 7.7724350 | 7.7814286 |
| 13 | 8 | 2.4576411 | 2.5573424 | 0.0000000 | 7.7842354 |

Figure 9:
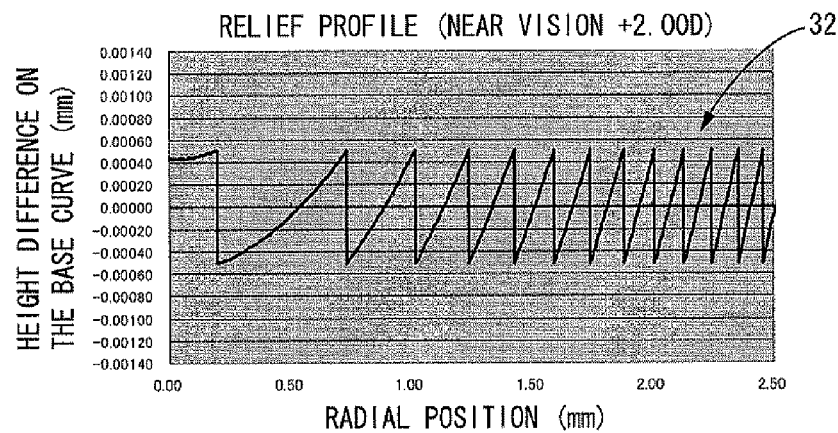
FIG. 9 is a relief profile of the relief for near vision, which composing the relief pattern.

As described above, curvature of the diffractive surface, geometric parameters such as the center position, and the relief profile of the relief 32 for near vision can be derived from the geometric relation. Table 1 shows geometric parameters of the relief 32 for near vision, and FIG. 9 shows the relief profile thereof.

Next, the relief form with the dioptric power at +1.00 D is designed as the relief 34 for intermediate vision. The relief 34 for intermediate vision needs to be designed by designing the first order light with a different focal distance from that of the relief 32 for near vision while synchronizing it with the relief 32 for near vision determined by the above procedure.

First, a formula for calculating a zone radius of the relief 34 for intermediate vision is defined as follows:

Zone radius=$((2M+A)\lambda(Nf))^{(1/2)}$ (5)

where M is a zone number, A is a zone constant, and N is a ratio of the focal distance of the relief for intermediate vision relative to that of the relief for near vision, which is expressed as:

(Focal distance of the relief for intermediate vision)/ (Focal distance of the relief for near vision).

Then, in order to synchronize the relief 32 for near vision and relief 34 for intermediate vision, assuming that a given zone of the relief 32 for near vision coincides with a given zone of the relief 34 for intermediate vision, the following equation is derived from the above equations (3) and (5):

$(((2m+a)\lambda f))^{(1/2)}=(((2M+A)\lambda(Nf)))^{(1/2)}$ which can be modified to obtain the following equation:

$A=(2(m-MN)+a)/N$ (6)

although A>0.

From the equation (6), the zone constant A is determined by the following equation, assuming that, for example, the zone No. 1 of the relief 32 for near vision synchronizes with the zone No. 0 of the relief 34 for intermediate vision:

$A=(2(1-0\times2)+0.16)/2=1.08$

The zone radius of the relief 34 for intermediate vision synchronized with the zone radius of the relief 32 for near vision is determined by the following equation:

Zone radius=$((2M+1.08)\lambda(Nf))^{(1/2)}$ (7)

TABLE 2

Relief for intermediate vision

| Zone No. | Curvature radius of virtual base curve | Zone origin (X-axis) | Zone terminal (X-axis) | Curvature center of Zone (Y-axis) | Zone curvature radius |
|---|---|---|---|---|---|
| 0 | 8 | 0.0000000 | 0.7348469 | 7.8727700 | 7.8728107 |
| 1 | 8 | 0.7348469 | 1.2409674 | 7.8740655 | 7.8751124 |
| 2 | 8 | 1.2409674 | 1.5937377 | 7.8760501 | 7.8780757 |
| 3 | 8 | 1.5937377 | 1.8814888 | 7.8780351 | 7.8810150 |
| 4 | 8 | 1.8814888 | 2.1307276 | 7.8800205 | 7.8839298 |
| 5 | 8 | 2.1307276 | 2.3537205 | 7.8820062 | 7.8868202 |
| 6 | 8 | 2.3537205 | 2.5573424 | 7.8839924 | 7.8896858 |
| 7 | 8 | 2.5573424 | 2.7459060 | 7.8859789 | 7.8925265 |
| 8 | 8 | 2.7459060 | 2.9223278 | 7.8879658 | 7.8953422 |
| 9 | 8 | 2.9223278 | 3.0886890 | 7.8899532 | 7.8981325 |
| 10 | 8 | 3.0886890 | 3.2465366 | 7.8919409 | 7.9008974 |
| 11 | 8 | 3.2465366 | 3.3970576 | 7.8939290 | 7.9036365 |
| 12 | 8 | 3.3970576 | 3.5411862 | 7.8959176 | 7.9063497 |
| 13 | 8 | 3.5411862 | 3.6796739 | 7.8979066 | 7.9090368 |

Figure 10:
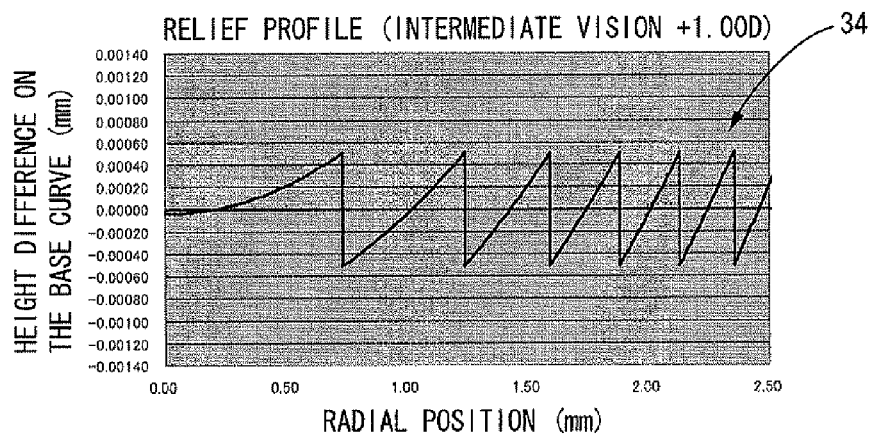
FIG. 10 is a relief profile of the relief for intermediate vision, which composing the relief pattern.

Besides, the height of the central relief and Y-axis value of the central apex can be determined in the same way as in the above relief 32 for near vision, whereas curvature of the diffractive surface, geometric parameters such as the center position, and the relief profile of the relief 34 for intermediate vision, which synchronizes with the relief 32 for near vision, are derived from the geometric relation. Table 2 shows geometric parameters of the relief 34 for intermediate vision, and FIG. 10 shows the relief profile thereof.

TABLE 3

Synchronized relief

| Zone No. | Curvature radius of virtual base curve | Zone origin (X-axis) | Zone terminal (X-axis) | Curvature center of Zone (Y-axis) | Zone curvature radius |
|---|---|---|---|---|---|
| 0 | 8 | 0.0000000 | 0.2000000 | 7.62917252623902 | 7.62878634737762 |
| 1 | 8 | 0.2000000 | 0.7348469 | 7.62975311751475 | 7.63038265007399 |
| 2 | 8 | 0.7348469 | 1.0198039 | 7.63284739659462 | 7.63548563522524 |
| 3 | 8 | 1.0198039 | 1.2409674 | 7.63478708706015 | 7.63841511245186 |
| 4 | 8 | 1.2409674 | 1.4282857 | 7.63853060066824 | 7.64411446633366 |

TABLE 3-continued

Synchronized relief

| Zone No. | Curvature radius of virtual base curve | Zone origin (X-axis) | Zone terminal (X-axis) | Curvature center of Zone (Y-axis) | Zone curvature radius |
|---|---|---|---|---|---|
| 5 | 8 | 1.4282857 | 1.5937377 | 7.64047099046897 | 7.64701906633684 |
| 6 | 8 | 1.5937377 | 1.7435596 | 7.64421693020352 | 7.65267073150148 |
| 7 | 8 | 1.7435596 | 1.8814888 | 7.64615802565085 | 7.65555033637838 |
| 8 | 8 | 1.8814888 | 2.0099751 | 7.64990641385506 | 7.66115406865168 |
| 9 | 8 | 2.0099751 | 2.1307276 | 7.65184822141825 | 7.66400855530817 |
| 10 | 8 | 2.1307276 | 2.2449944 | 7.65559908099775 | 7.66956410003856 |
| 11 | 8 | 2.2449944 | 2.3537205 | 7.65754160730963 | 7.67239333999525 |
| 12 | 8 | 2.3537205 | 2.4576411 | 7.66129496175732 | 7.67790043165719 |
| 13 | 8 | 2.4576411 | 2.5573424 | 7.66323821362182 | 7.68070429084488 |

Figure 11:
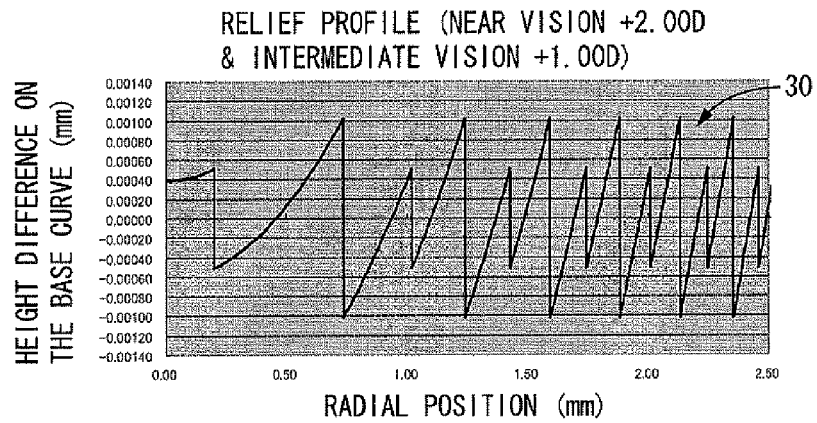
FIG. 11 is a relief profile of the relief pattern.

Subsequently, a relief profile of the relief pattern 30 having a synchronous structure where the relief 32 for near vision and relief 34 for intermediate vision are periodically overlapped is completed by combining the relief profiles of the relief 32 for near vision and the relief 34 for intermediate vision. Table 3 shows geometric parameters of the relief pattern 30 and FIG. 11 shows the relief profile thereof.

Then, according to the relief profile obtained, the relief pattern 30 is formed on the rear optical part 24. Formation of the relief pattern 30 on the rear optical part 24 is made not only by molding but also by machining and the like including laser processing, etching and cutting as appropriate. The contact lens 10 according to the above embodiment is obtained this way.

Embodiments and manufacturing methods of this invention have been described thus far, but these are just examples, and this invention is not to be interpreted in a limited sense by any specific description of such embodiments. Several other aspects that can be preferably adopted in this invention will be shown below, although it should be understood that this invention is not limited to those aspects. In the descriptions below, details are omitted by applying the same reference numerals as those of the above embodiments to similar materials and parts to those thereof.

Figure 12:
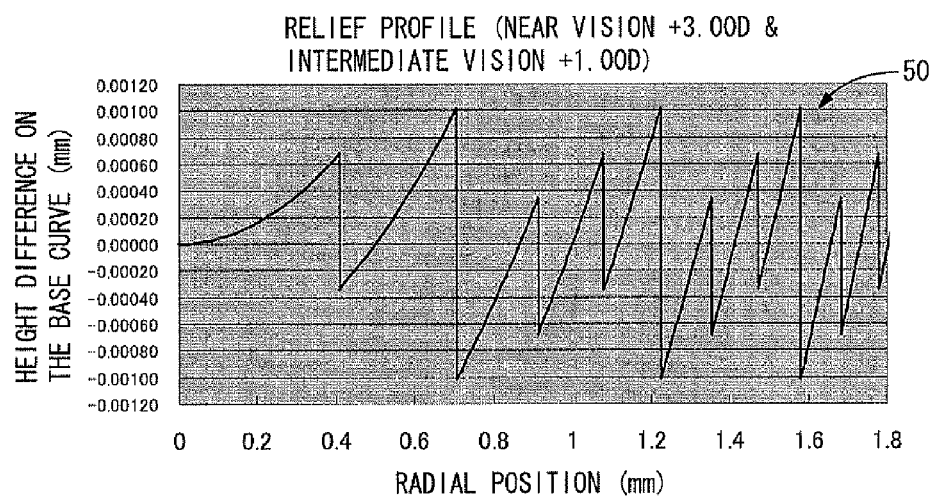
FIG. 12 is a relief profile of a relief pattern as a second embodiment of this invention.

First, FIG. 12 shows a relief profile of a relief pattern 50 as a second embodiment of this invention. In the present embodiment, a synchronous structure is set up where two reliefs with the dioptric power at +3.0 D for near vision and the other at +1.0 D for intermediate vision are periodically overlapped. By the way, the relief profile of the present embodiment is the one obtained under the following conditions:

Radius of the base curve of the rear optical part=8.000 mm
Dioptric power of the rear optical part=+5.0 D
Refractive index of the lens material=1.500
Refractive index of the surrounding medium=1.336
Designed wavelength=500 nm
Zone constant of the relief for near vision 'a'=1

Meanwhile, the grating pitch is larger in the relief for intermediate vision than in the relief for near vision.

Especially in the present embodiment, two relief depths of the relief for near vision are provided per each zone of the relief for intermediate vision, and these three zones in total are formed, that is, in one out of three zone radii of the relief for near vision, the zone radius of the relief for intermediate vision is made equal to that of the relief for near vision. And, in each zone of the relief for intermediate vision composed of an overlap of reliefs for near vision, the height of the relief depth of the relief for near vision located between the relief depths of the relief for intermediate vision relative to the virtual base curve surface is made to vary gradually in the zone direction (left-right direction in FIG. 12), and in the present embodiment, the height is made to gradually increase moving away from the center in the zone direction. Such relief pattern 50 can also be formed according to the same manufacturing method as the above first embodiment.

Figure 13:
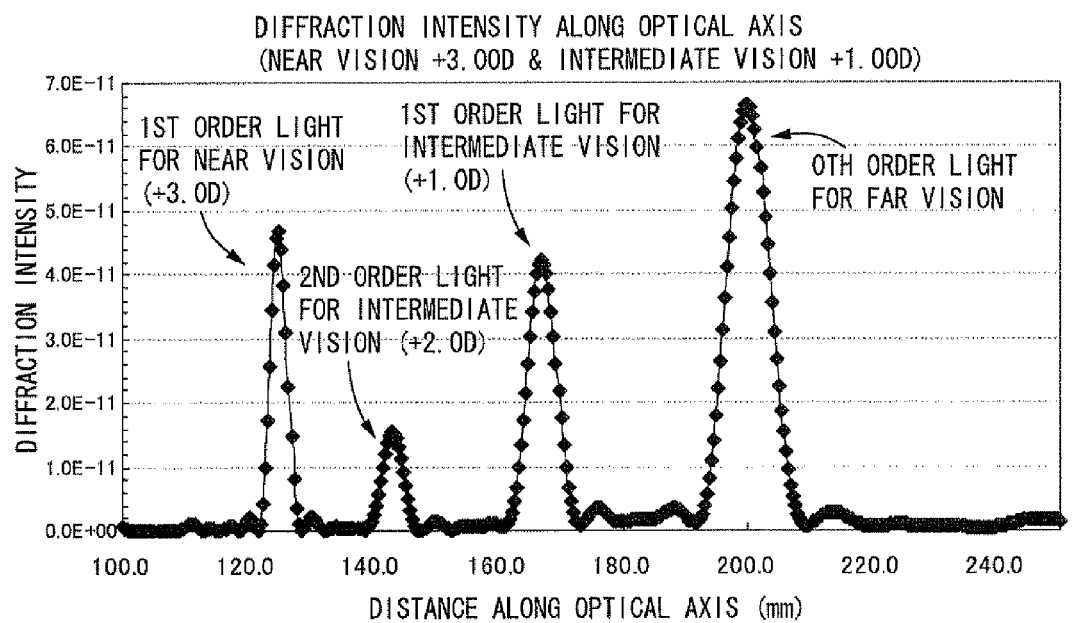
FIG. 13 is a graph showing a simulation result of diffraction intensity in the relief pattern.

Also, FIG. 13 shows a result of computer simulation of diffraction intensity along the optical axis obtained by the relief pattern 50 according to the present embodiment, just like the above first embodiment. As evident from FIG. 13, also in the present embodiment, it was confirmed that a peak of diffraction intensity is generated at the focus for intermediate vision of the first order diffracted light by the relief for intermediate vision between the focus for far vision of the 0th order light by the refractive surface and the focus for near vision of the first order diffracted light by the relief for near vision, and a peak is clearly generated in each of far, near and intermediate vision ranges.

In addition, especially in the present embodiment, the second order diffracted light of the relief for intermediate vision is generated. Thus, by changing the design parameters of the relief pattern 50, it is possible to generate multiple foci for intermediate vision. Also, peak intensity and focal position of the diffracted light can be set in various aspects by means of, for example, further adding a relief that periodically overlaps with the relief pattern 50 having a synchronous structure.

Figure 14:
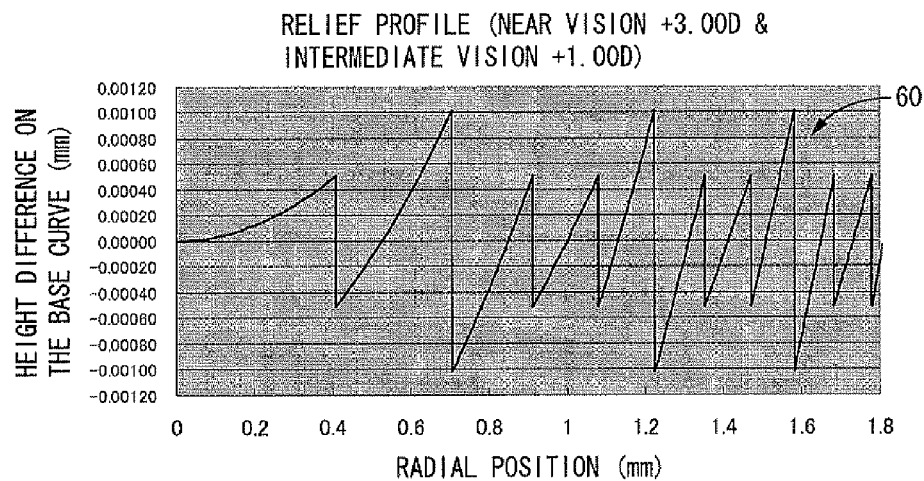
FIG. 14 is a relief profile of a relief pattern as a third embodiment of this invention.

Next, FIG. 14 shows a relief profile of a relief pattern 60 as a third embodiment of this invention. In the present embodiment, a synchronous structure is set up where two reliefs with the dioptric power at +3.0 D for near vision and at +1.0 D for intermediate vision are periodically overlapped. Meanwhile, the grating pitch is larger in the relief for intermediate vision than in the relief for near vision.

In the present embodiment, two relief depths of the relief for near vision are provided per each zone of the relief for intermediate vision, and these three zones in total are formed, that is, in one out of three zone radii of the relief for near vision, the zone radius of the relief for intermediate vision is made equal to that of the relief for near vision. And, in each zone of the relief for intermediate vision composed of an overlap of reliefs for near vision, the height of the relief depth of the relief for near vision located between the relief depths of the relief for intermediate vision relative to the virtual base curve surface is kept approximately constant in the zone direction (left-right direction in FIG. 14).

Such relief pattern 60 can be manufactured by an easier method than the above first and second embodiments. In other words, a relief pattern with a synchronous structure can be easily obtained by means of increasing the relief depth where the relief with a smaller grating pitch is overlapped with the one with a larger grating pitch based on the overlapping cycle of multiple reliefs on top of each other. For example, the dioptric power of the reliefs for near vision and intermediate vision in the present embodiment are the same as those of the above second embodiment, but as evident from the second embodiment (see FIG. 12), the relief for intermediate vision is synchronized with the relief for near vision once in every three times. Therefore, after designing the relief form for near vision according to the above manufacturing method, a relief form similar to that of the second embodiment can be obtained easily by means of increasing the relief depth of the obtained relief form for near vision once in every three times without exactly designing the relief form for intermediate vision like the above manufacturing method.

Figure 15:
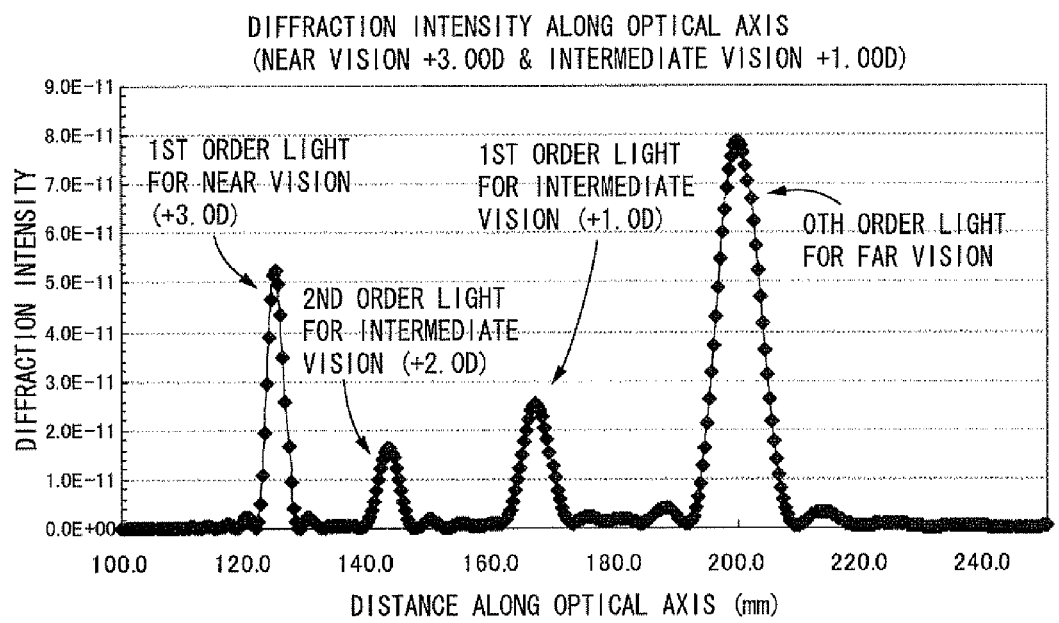
FIG. 15 is a graph showing a simulation result of diffraction intensity in the relief pattern.

Also, FIG. 15 shows a result of computer simulation of diffraction intensity along the optical axis obtained by the relief pattern 60 according to the present embodiment, as was done in the above first embodiment. As evident from FIG. 15, despite that diffraction intensity for intermediate vision drops slightly as opposed to the above second embodiment (see FIG. 13), it was confirmed that an effect similar to that of the above second embodiment can be achieved by generating a peak of diffraction intensity at the focus for intermediate vision by an easy manufacturing method according to the present embodiment.

Figure 16:
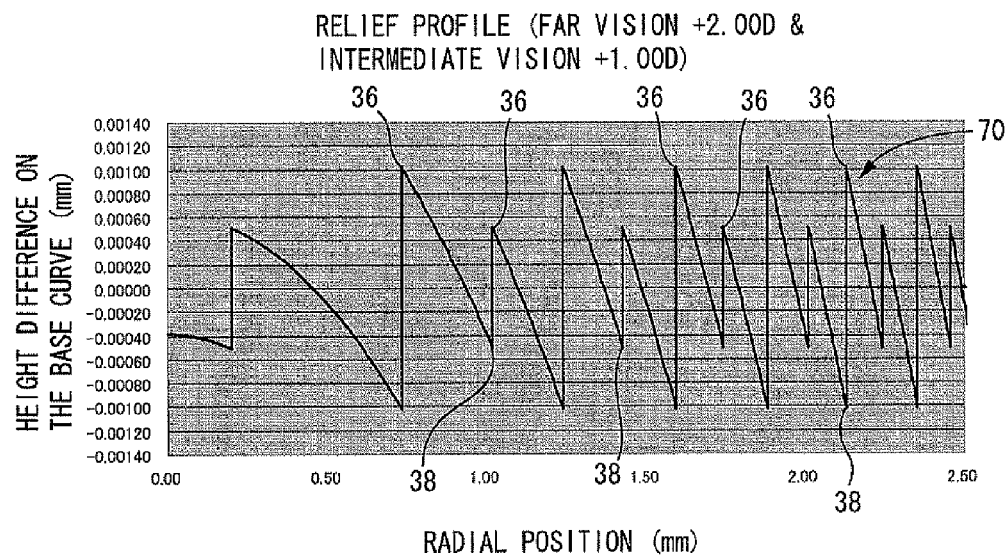
FIG. 16 is a relief profile of a relief pattern as a fourth embodiment of this invention.

Next, FIG. 16 shows a relief pattern 70 in profile as a fourth embodiment of this invention. In the present embodiment, a synchronous structure is set up where two reliefs with the dioptric power at +2.0 D for far vision and at +1.0 D for intermediate vision are periodically overlapped. Meanwhile, the grating pitch is larger in the relief for intermediate vision than in the relief for far vision.

As evident from FIG. 16, the relief pattern 70 of the present embodiment has its depth with the positive and negative reversed from that of relief pattern 30 (see FIG. 11) in the above first embodiment, and the ridge line 36 is positioned closer to the center than the valley line 38 in each zone. According to the present embodiment, the 0th order light of the refractive surface is set to focus for near vision and the negative first order light of the relief for far vision is set to focus for far vision, while the negative first order light of the relief for intermediate vision is set to focus for intermediate vision. And as described above, the first order diffracted light of this invention is to be interpreted as first order light with an absolute value including the negative first order light.

Figure 17:
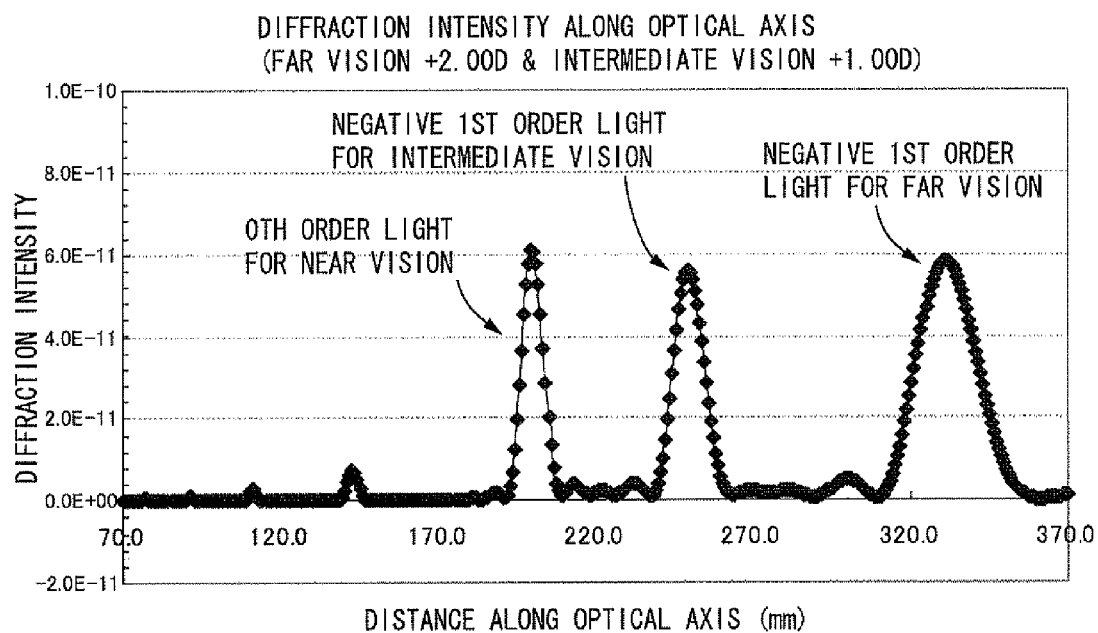
FIG. 17 is a graph showing a simulation result of diffraction intensity in the relief pattern.

Also, FIG. 17 shows a computer simulation result of diffraction intensity along the optical axis obtained by the relief pattern 70 according to the present embodiment, as was done in the above first embodiment. As evident from FIG. 17, according to the present embodiment, a peak of diffraction intensity at the focus for far vision by the negative first order light of the relief for far vision is generated in addition to that at the focus for near vision by the 0th order light of the refractive surface, while a peak of diffraction intensity at the focus for intermediate vision by the negative first order light of the relief for intermediate vision is generated between these foci for near vision and far vision. Also, it was confirmed that a peak can be clearly generated in each of far, near and intermediate vision ranges in the present embodiment, too.

Figure 18:
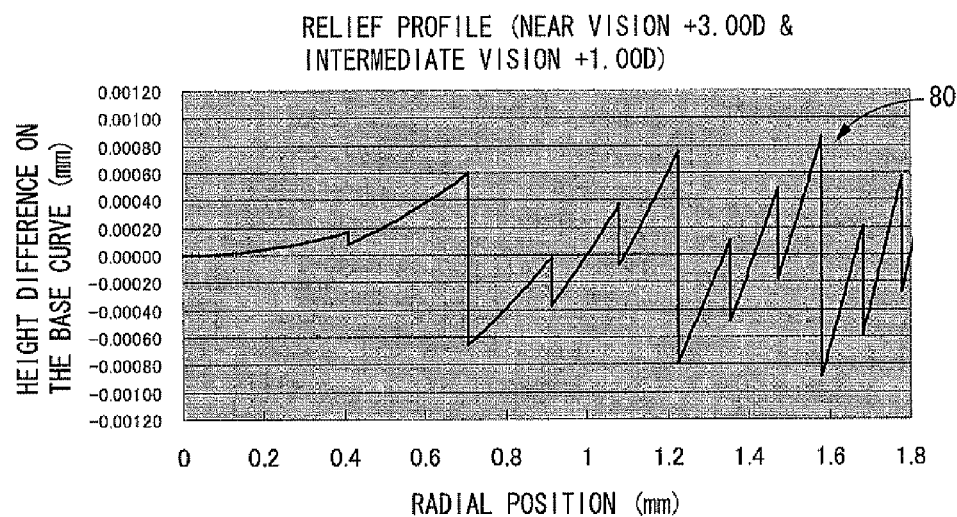
FIG. 18 is a relief profile of a relief pattern as a fifth embodiment of this invention.

Next, FIG. 18 shows a relief pattern 80 in profile as a fifth embodiment of this invention. In the present embodiment, a synchronous structure is set up where two reliefs with the dioptric power at +3.0 D for near vision and at +1.0 D for intermediate vision are periodically overlapped. Meanwhile, the grating pitch is larger in the relief for intermediate vision than in the relief for near vision.

The relief pattern 80 of the present embodiment is in a similar form to that of the relief pattern 50 (see FIG. 12) as the above second embodiment, and especially in the present embodiment, only the relief component for near vision is made to increase outward from the center at zero as compared to the relief pattern 50 as the above second embodiment. This makes it possible to reduce diffractive intensity for near vision.

Figure 19:
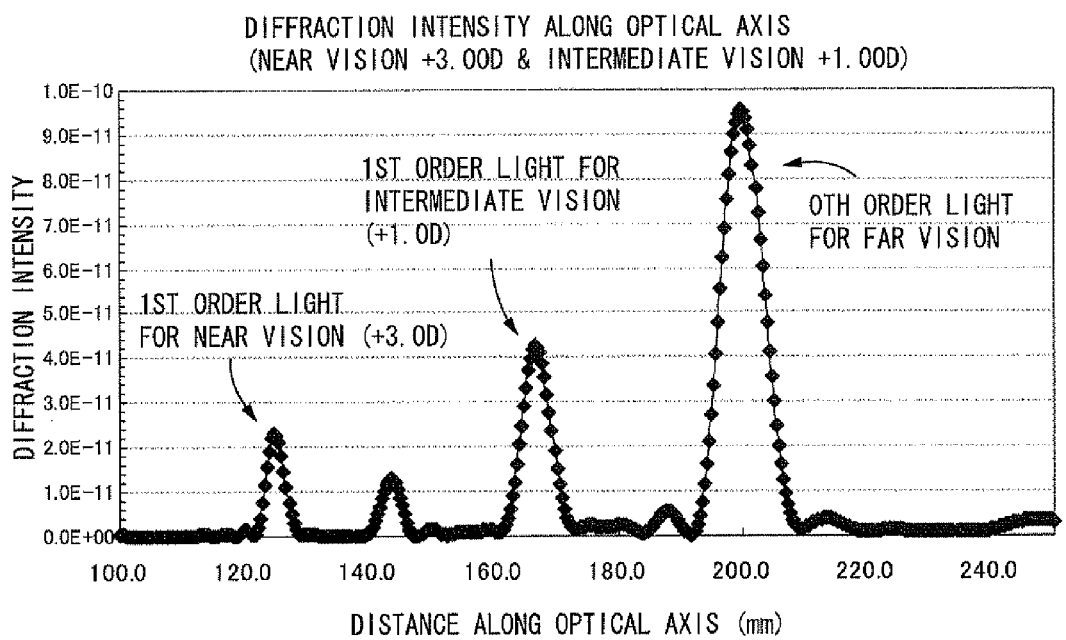
FIG. 19 is a graph showing a simulation result of diffraction intensity in the relief pattern.

Also, FIG. 19 shows a computer simulation result of diffractive intensity along the optical axis obtained by the relief pattern 80 according to the present embodiment, as was done in the above first embodiment. As evident from FIG. 19, it is confirmed that a peak of diffraction intensity at the focus for near vision can be reduced, according to the present embodiment, as compared to the above second embodiment (see FIG. 13).

Also, in each of the above embodiments, a diffraction grating with a synchronous structure where multiple reliefs are periodically overlapped was formed on the rear optical part of the contact lens, but such a diffraction grating to be formed in at least a part of the area in the radial direction of the diffraction lens, for example, only in the middle of the rear optical part in the radial direction, while only one type of relief is formed in the other part of the area. For example, in case of the relief pattern 30 formed on the contact lens 10 as the above first embodiment, the diffraction grating with a synchronous structure can be formed all over the lens including the rear optical part and its periphery. Furthermore, it is of course possible to form the diffraction grating with such structure on the front optical part.

Figure 20:
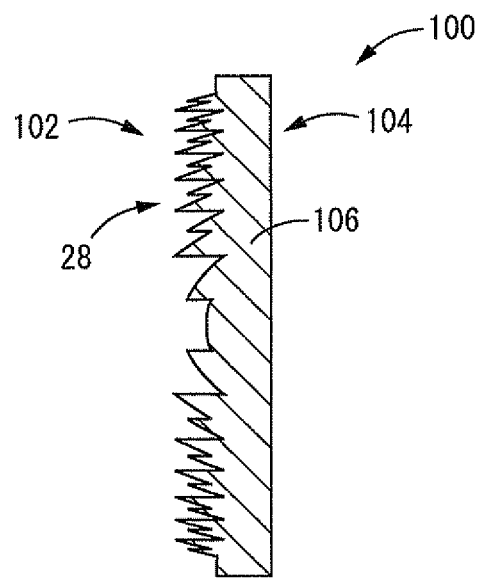
FIG. 20 is a cross-section diagram showing a diffraction lens as a different aspect of this invention.
Figure 21:
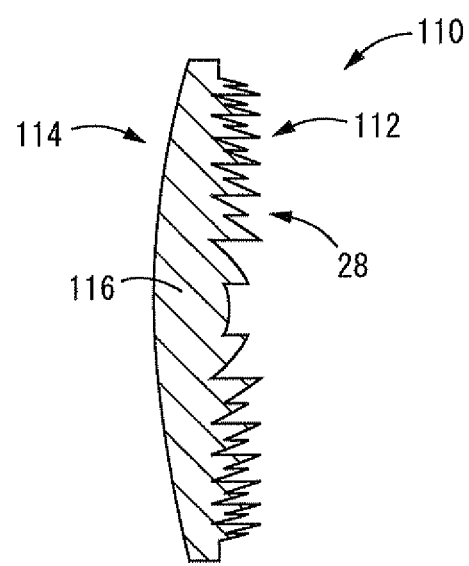
FIG. 21 is a cross-section diagram showing a diffraction lens as a further different aspect of this invention.

Additionally, the surface of the optical material where the diffraction grating with a synchronous structure is formed is not limited to refractive surfaces. For example, as shown diagrammatically in FIG. 20, the diffraction grating 28 can be formed on a plane 102, one of the two planes 102 and 104 of an optical material 106, like a diffraction lens 100 as a different aspect of this invention, or as shown diagrammatically in FIG. 21, the diffraction grating 28 can even be formed on a plane 112 of an optical material 116 where one surface is the flat plane 112 and the other is a curved plane 114 as refractive surface, like a diffraction lens 110 as a further different aspect of this invention.

Furthermore, for the purpose of reducing aberration, it is possible to form a diffraction grating according to this invention, for example, on a surface of a laminate of two materials with different dispersion, as described in the bulletin of JP-A-2001-42112.

Also, in each of the above embodiments, a contact lens was exemplified as a diffraction lens, but as diffraction lenses of this invention, not only ophthalmic lenses for vision corrections such as glasses and phakic intraocular lenses including phakic IOLs and ICLs and the like, for example, but also optical lenses used for ophthalmic inspection devices and various optical devices including cameras and optical disc pickups can be adopted, as appropriate. Therefore, as the optical materials for this invention, optical transparent materials such as resin and glass can be adopted, as appropriate.

Moreover, the cornea can be considered as one of the optical lenses, and it is also possible to apply the present manufacturing method, for example, to surgery operations for reconstruction of the corneal surface by Lasik. In other words, it is possible to set a relief pattern with a synchronous structure according to the above manufacturing method, and then provide the set relief pattern on the cornea by laser processing and the like.

TABLE 4

Relief for near vision

| Zone No. | Curvature radius of virtual base curve | Zone origin (X-axis) | Zone terminal (X-axis) | Curvature center of Zone (Y-axis) | Zone curvature radius |
|---|---|---|---|---|---|
| 0 | 8 | 0.0000000 | 0.2000000 | −7.6287218 | 7.62808153675024 |
| 1 | 8 | 0.2000000 | 0.7348469 | −7.6295553 | 7.63043867104098 |
| 2 | 8 | 0.7348469 | 1.0198039 | −7.6323956 | 7.63478300097590 |
| 3 | 8 | 1.0198039 | 1.2409674 | −7.6352365 | 7.63910928344434 |
| 4 | 8 | 1.2409674 | 1.4282857 | −7.6380783 | 7.64341747569116 |
| 5 | 8 | 1.4282857 | 1.5937377 | −7.6409208 | 7.64770753403725 |
| 6 | 8 | 1.5937377 | 1.7435596 | −7.6437642 | 7.65197941386086 |
| 7 | 8 | 1.7435596 | 1.8814888 | −7.6466083 | 7.65623306958273 |
| 8 | 8 | 1.8814888 | 2.0099751 | −7.6494532 | 7.66046845464634 |
| 9 | 8 | 2.0099751 | 2.1307276 | −7.6522989 | 7.66468552150125 |
| 10 | 8 | 2.1307276 | 2.2449944 | −7.6551454 | 7.66888422158524 |
| 11 | 8 | 2.2449944 | 2.3537205 | −7.6579927 | 7.67306450530204 |
| 12 | 8 | 2.3537205 | 2.4576411 | −7.6608408 | 7.67722632200566 |
| 13 | 8 | 2.4576411 | 2.5573424 | −7.6636897 | 7.68136961997595 |

Figure 22:
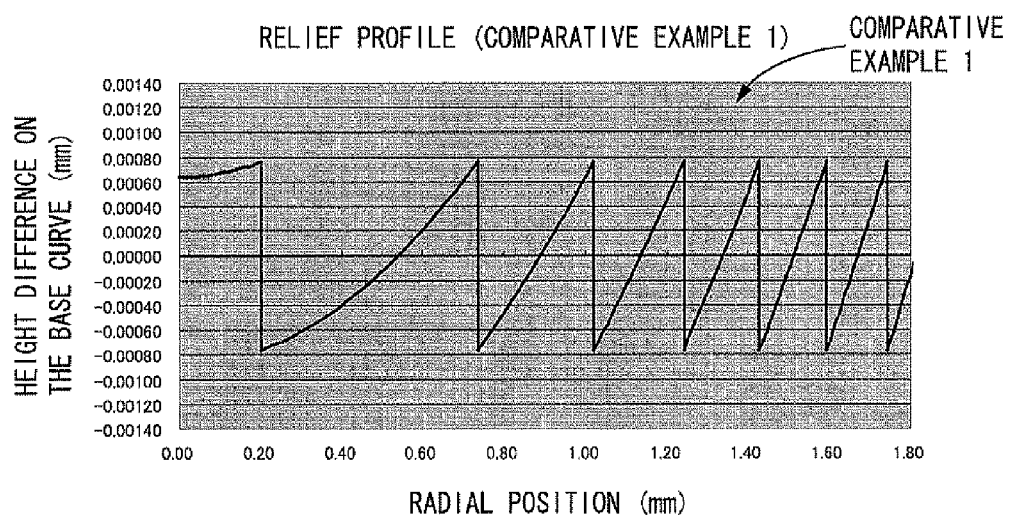
FIG. 22 is a relief profile showing a relief pattern according to a conventional structure.
Figure 23:
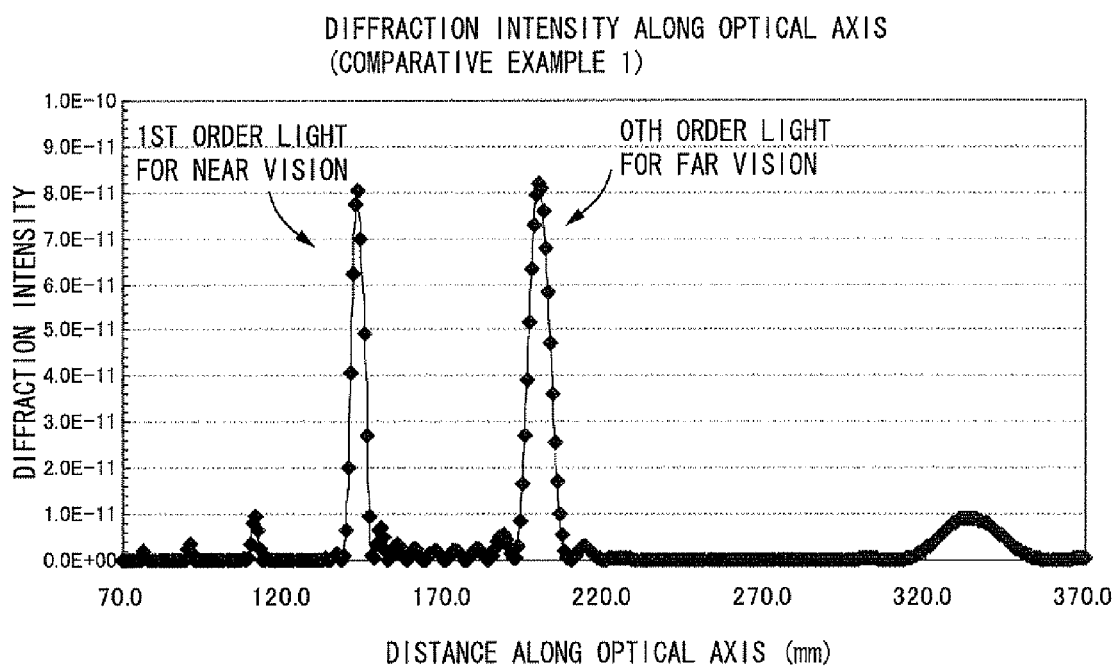
FIG. 23 is a graph showing a simulation result of diffraction intensity in the relief pattern.

Also, as the comparative example 1 as compared to the working example according to the above first embodiment (see FIG. 7), a computer simulation has been performed of diffraction intensity obtained by a relief pattern of a bifocal lens according to the conventional structure. Table 4 shows geometric parameters of the comparative example 1 and FIG. 22 shows a relief profile thereof. The relief pattern of the comparative example 1 was set at a dioptric power of +2.00 D for near vision. A result of such simulation is shown in FIG. 23. As is publicly known, in the comparative example 1 according to the conventional structure, it is confirmed that only two peaks can be generated, one by the 0th order light of the refractive surface and the other by the first order diffracted light of the relief for near vision, unlike the working example.

Figure 24A:
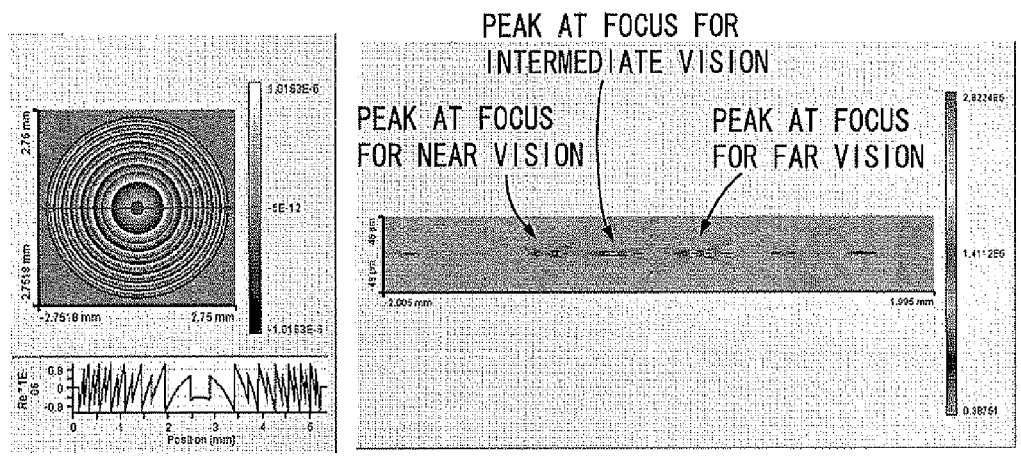
FIGS. 24A and 24B show simulation results of diffraction intensity of relief patterns with a structure according to this invention and a structure according to the prior art.
Figure 24B:
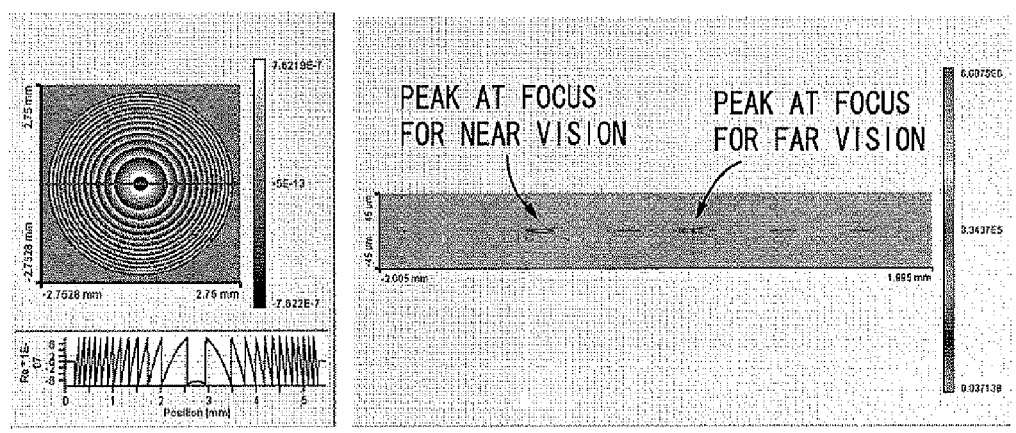

In addition, in order to enhance the reliability of the simulation result, generation of peaks of diffraction intensity was verified for the relief pattern according to the working example and the relief pattern according to the comparative example 1 using an wave-optical design and analysis software (VirtualLab, a brand name of LightTrans). Such verifications are shown in FIG. 24A for the working example and in FIG. 24B for the comparative example 1. As evident from FIGS. 24A and 24B, it was also confirmed in this simulation, according to the working example with a structure following this invention, that an intensive peak of diffraction intensity at the focus for intermediate vision is generated between the foci for far vision and near vision, unlike in the conventional structure.

Figure 25:
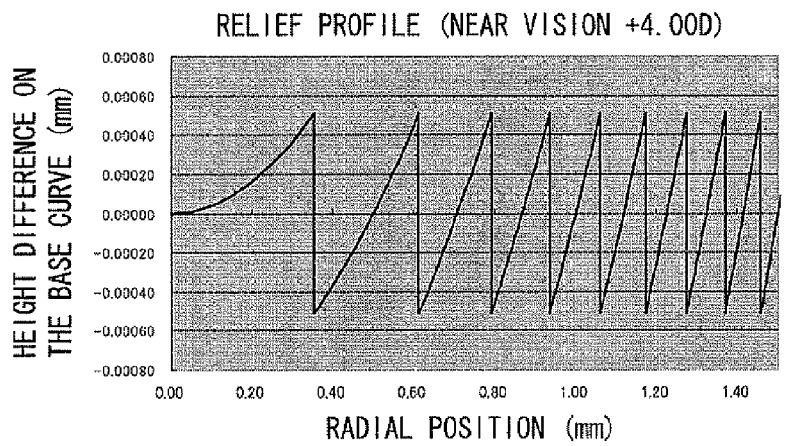
FIG. 25 is a relief profile of a relief for near vision, which composing a relief pattern as a comparative example 2.
Figure 26:
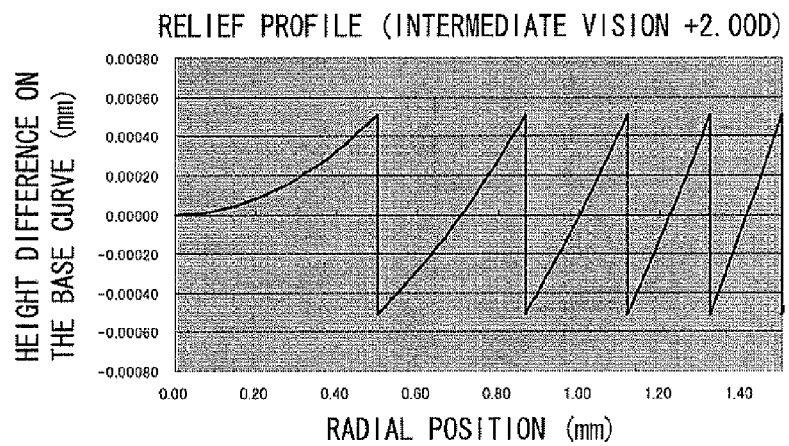
FIG. 26 is a relief profile of a relief for intermediate vision, which composing the relief pattern as the comparative example 2.
Figure 27:
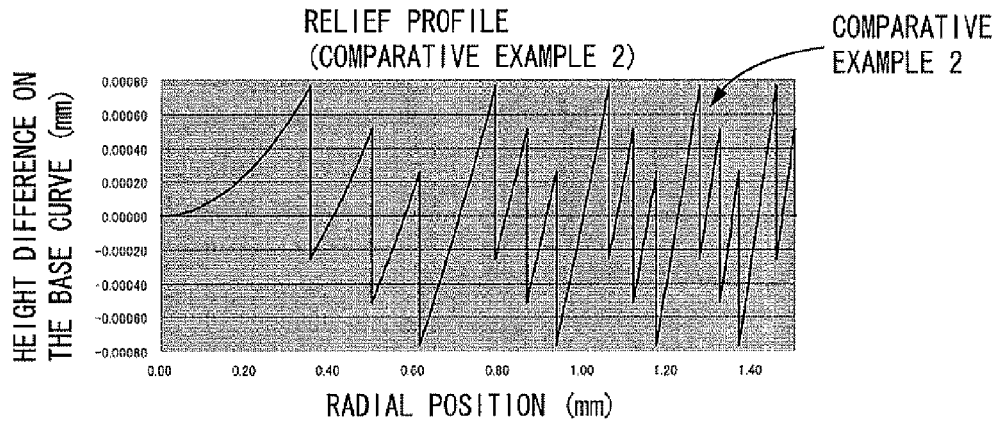
FIG. 27 is a relief profile showing the relief pattern as the comparative example 2.
Figure 28:
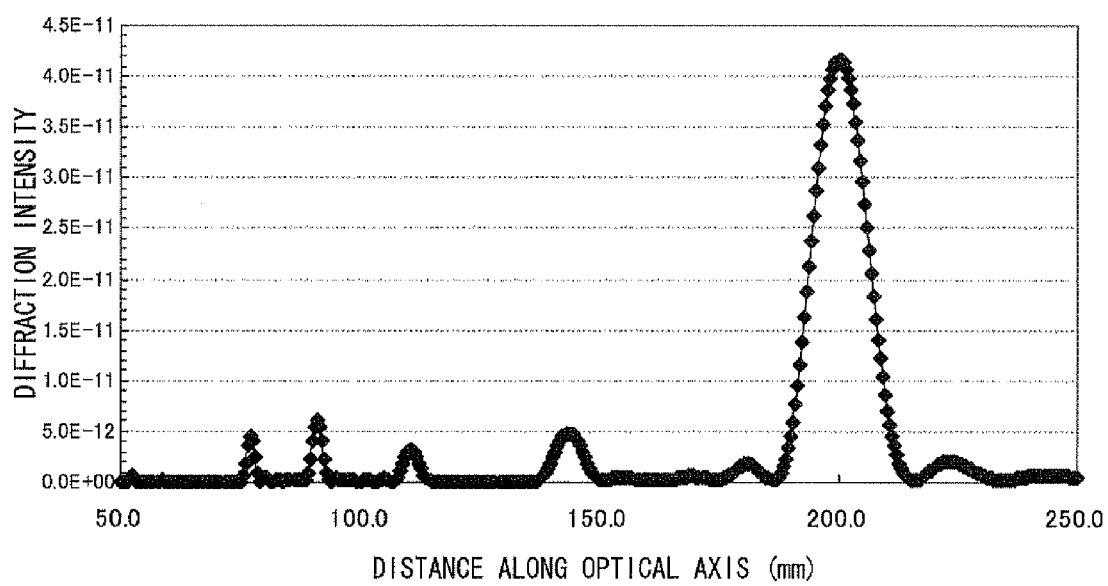
FIG. 28 is a graph showing a simulation result of diffraction intensity of the relief pattern.

Also, as a comparative example 2, a contact lens having a relief pattern with an asynchronous structure where the reliefs for near vision and intermediate vision are simply overlapped with no synchronization was prepared. In this comparative example 2, a relief pattern was set to have its dioptric power at +5.0 D, curvature radius of the base curve at 8.000 mm, refractive index of the lens material at 1.500, refractive index of the surrounding medium at 1.336, and design wavelength at 500 nm, while the relief for near vision with the dioptric power at +4.00 D and the relief for intermediate vision with the dioptric power at +2.00 D, with each zone constant set at 1, were overlapped in an asynchronous form. FIGS. 25 and 26 show the relief profiles of the relief for near vision and intermediate vision, respectively. FIG. 27 shows, as the comparative example 2, a relief profile which is an overlap of these reliefs for near vision and intermediate vision with no synchronization, while FIG. 28 shows a simulation result of diffraction intensity obtained by the relief pattern of said comparative example 2. As evident from FIG. 28, in the comparative example 2 which is a simple overlap of multiple relief patterns, it was confirmed that no obvious generation of peaks was detected in any of the 0th order light by the refractive surface, the first order diffractive light by the relief for near vision, or the first order diffractive light by the relief for intermediate vision, causing to generate peaks of unintended order of light. This revealed the usefulness of this invention wherein a synchronous structure is set where multiple reliefs are periodically overlapped.

The invention claimed is:

1. A manufacturing method of a diffraction lens other than an aphakic intraocular lens provided with a diffraction grating having a relief pattern extending concentrically on a surface of an optical material, the method comprising the steps of:
adopting various types of reliefs whose first order diffracted lights give respective focal distances different from one another for the relief pattern;
setting up a synchronous structure where (1) at least two reliefs are set to overlap with each other in at least a part of an area in a radial direction of the diffraction lens, and (2) grating pitches of an other relief are overlapped periodically with respect to every grating pitch of one relief having a maximum grating pitch among the reliefs set up in overlap in order to obtain a resulting relief pattern; and
forming the resulting relief pattern on the surface of the optical material,
wherein the various types of reliefs are arranged to satisfy a following equation:

$$A=(2(m-N*M)+a)/N$$

where A is a zone constant of the one relief, 'a' is a zone constant of the other relief, M is a zone number of the one relief, m is a zone number of the other relief, and N is a ratio of a focal distance of the one relief relative to that of the other relief, which is expressed as:

(focal distance of the one relief)/(focal distance of the other relief).

2. The manufacturing method of a diffraction lens according to claim 1, wherein the optical material comprises an optical lens with a refractive surface, and
the method further comprising the step of setting a focal distance for a 0th order light by the refractive surface of the lens to be a focal distance different from that of any of the first order diffracted lights generated by the various types of reliefs.

3. The manufacturing method of a diffraction lens according to claim 1, further comprising the step of overlapping the reliefs to set each relief depth of the relief having the maximum grating pitch to be constant in a zone direction.

4. The manufacturing method of a diffraction lens according to claim 3, further comprising the steps of:
forming, in each zone in the relief having the maximum grating pitch, another type of relief with at least two relief depths in the area in the radial direction of the lens where the various types of reliefs are set up in overlap; and
setting dimensions of the at least two relief depths relative to a virtual base curve surface so as to gradually vary in the zone direction.

5. The manufacturing method of a diffraction lens according to claim 3, further comprising the steps of:
forming, in each zone in the relief having the maximum grating pitch, another type of relief with at least two relief depths in the area in the radial direction of the lens where the various types of reliefs are set up in overlap; and
setting dimensions of the at least two relief depths relative to a virtual base curve surface so as to be constant in the zone direction.

6. The manufacturing method of a diffraction lens according to claim 1, wherein the optical material comprises an ophthalmic lens with a refractive surface, and the method further comprises the steps of:
setting the diffraction grating composed of the various types of reliefs on the refractive surface, the refractive surface being in a concave shape, and
in at least one type of the reliefs in a radial cross-section, setting an inclination direction between zones outward along a lens axis in a same direction as a protrusion of a relief depth.

7. The manufacturing method of a diffraction lens according to claim 1, wherein the various types of reliefs are arranged to satisfy a following equation:

$$D \leq \lambda/(N_{lens} - N_{med})$$

where D is a dimension of a relief depth, $\lambda$ is a design wavelength, $N_{lens}$ is a refractive index of the optical material, and $N_{med}$ is a refractive index of a surrounding medium.

8. A diffraction lens other than an aphakic intraocular lens provided with a diffraction grating having a relief pattern extending concentrically on a surface of an optical material, the diffraction lens comprising:
a synchronous structure where (1) various types of reliefs including at least two reliefs that are set to overlap with each other in at least a part of an area in a radial direction of the lens, the at least two reliefs having first order diffracted lights that give respective focal distances different from one another, and (2) grating pitches of an other relief being overlapped periodically with respect to every grating pitch of one relief having a maximum grating pitch among the reliefs set up in overlap,
wherein the various types of reliefs are arranged to satisfy a following equation:

$$A = (2(m - N*M + a))/N$$

where A is a zone constant of the one relief, 'a' is a zone constant of the other relief, M is a zone number of the one relief, m is a zone number of the other relief, and N is a ratio of a focal distance of the one relief relative to that of the other relief, which is expressed as:

(focal distance of the one relief)/(focal distance of the other relief).

9. The diffraction lens according to claim 8, wherein the optical material comprises an optical lens with a refractive surface, and a focal distance is set for a 0th order light by the refractive surface of the lens to be different from that of any of the first order diffracted lights generated by the various types of reliefs.

10. The diffraction lens according to claim 8, wherein each relief depth of the relief having the maximum grating pitch is made constant in a zone direction.

11. The diffraction lens according to claim 10, wherein in each zone in the relief having the maximum grating pitch,
another type of relief with at least two relief depths is formed in the area in the radial direction of the lens where the various types of reliefs are set up in overlap, and
dimensions of the at least two relief depths relative to a virtual base curve surface vary gradually in the zone direction.

12. The diffraction lens according to claim 10, wherein in each zone in the relief having the maximum grating pitch,
another type of relief with at least two relief depths is formed in the area in the radial direction of the lens where the various types of reliefs are set up in overlap, and
dimensions of the at least two relief depths relative to a virtual base curve surface are set constant in the zone direction.

13. The diffraction lens according to claim 8, wherein the optical material comprises an ophthalmic lens with a refractive surface, the diffraction grating composed of the various types of reliefs is set on the refractive surface, the refractive surface being in a concave shape, and in at least one type of the reliefs in a radial cross-section, an inclination direction between zones is set outward along a lens axis in a same direction as a protrusion of a relief depth.

14. The diffraction lens according to claim 8, wherein the various types of reliefs are arranged to satisfy a following equation:

$$D \leq \lambda/(N_{lens} - N_{med})$$

where D is a dimension of a relief depth, $\lambda$ is a design wavelength, $N_{lens}$ is a refractive index of the optical material, and $N_{med}$ is a refractive index of a surrounding medium.

* * * * *